(12) United States Patent
Matsumoto et al.

(10) Patent No.: US 9,110,052 B2
(45) Date of Patent: Aug. 18, 2015

(54) BIOLOGICAL INFORMATION, ACQUISITION METHOD AND INSTRUMENT, AND PHYSIOLOGICALLY-ACTIVE SUBSTANCE MEASUREMENT METHOD AND INSTRUMENT

(75) Inventors: Masahiro Matsumoto, Kanagawa (JP); Tomoko Katsuhara, Kanagawa (JP); Yuuki Watanabe, Kanagawa (JP); Masatsugu Ueno, Tokyo (JP); Tomohiko Nakamura, Tokyo (JP); Sayaka Chikuma, Kanagawa (JP)

(73) Assignee: Sony Corporation, Tokyo (JP)

( * ) Notice: Subject to any disclaimer, the term of this patent is extended or adjusted under 35 U.S.C. 154(b) by 1125 days.

(21) Appl. No.: 12/469,273

(22) Filed: May 20, 2009

(65) Prior Publication Data

US 2009/0292183 A1 Nov. 26, 2009

(30) Foreign Application Priority Data

| May 20, 2008 | (JP) | ................................. | 2008-131752 |
| Oct. 30, 2008 | (JP) | ................................. | 2008-279360 |
| Apr. 17, 2009 | (JP) | ................................. | 2009-100582 |
| May 1, 2009 | (JP) | ................................. | 2009-111993 |

(51) Int. Cl.
*A61B 5/00* (2006.01)
*A61B 10/00* (2006.01)
*G01N 33/52* (2006.01)
*B01L 3/00* (2006.01)

(52) U.S. Cl.
CPC ............ *G01N 33/52* (2013.01); *A61B 10/0064* (2013.01); *B01L 3/502715* (2013.01); *A61B 10/0012* (2013.01); *B01L 3/502738* (2013.01); *B01L 2200/027* (2013.01); *B01L 2200/0605* (2013.01); *B01L 2400/065* (2013.01)

(58) Field of Classification Search
None
See application file for complete search history.

(56) References Cited

U.S. PATENT DOCUMENTS

| 5,438,984 A | * | 8/1995 | Schoendorfer | ................ 600/573 |
| 2003/0225362 A1 | * | 12/2003 | Currie et al. | .................... 604/20 |
| 2004/0162467 A1 | * | 8/2004 | Cook | ............................ 600/309 |

FOREIGN PATENT DOCUMENTS

| JP | 04-256756 | | 9/1992 |
| JP | 04-367653 | | 12/1992 |
| JP | 08-504513 | | 5/1996 |
| JP | 10-221221 | | 8/1998 |
| JP | 11-038004 | | 2/1999 |
| JP | 2000-131318 | | 5/2000 |
| JP | 2000-505334 | A | 5/2000 |
| JP | 2000-287942 | | 10/2000 |
| JP | 2004-529734 | A | 9/2004 |
| JP | 2005-083510 | A | 3/2005 |
| JP | 2005-083945 | A | 3/2005 |
| JP | 2006-094969 | | 4/2006 |
| JP | 2007-108140 | A | 4/2007 |
| WO | WO 2006/018044 | A1 | 2/2006 |
| WO | WO 2006/047290 | A2 | 5/2006 |
| WO | WO 2006047290 | A2 * | 5/2006 |
| WO | WO 2007/066484 | A1 | 6/2007 |

* cited by examiner

*Primary Examiner* — H. Sarah Park
(74) *Attorney, Agent, or Firm* — Wolf, Greenfield & Sacks, P.C.

(57) ABSTRACT

A biological information acquisition method for acquiring information on a living body on a basis of a quantified value of a physiologically active substance originated from the living body, includes a step of collecting the physiologically active substance from a body surface of the living body.

17 Claims, 13 Drawing Sheets

◆day1, ■day2, ▲day3, ●day4

BIOLOGICAL INFORMATION, ACQUISITION METHOD AND INSTRUMENT, AND PHYSIOLOGICALLY-ACTIVE SUBSTANCE MEASUREMENT METHOD AND INSTRUMENT

CROSS REFERENCE TO RELATED APPLICATIONS

The present applications claims priority under 35 U.S.C. §119 to Japanese Patent Application No. JP 2009-111993, filed in the Japan Patent Office on May 1, 2009, to Japanese Patent Application No. JP 2009-100582, filed in the Japan Patent Office on Apr. 17, 2009, to Japanese Patent Application No. JP 2008-279360, filed in the Japan Patent Office on Oct. 30, 2008, and to Japanese Patent Application No. JP 2008-131752, filed in the Japan Patent Office on May 20, 2008. The entire contents of each of which are incorporated herein by reference.

BACKGROUND OF THE INVENTION

1. Field of the Invention

This invention relates to a biological information acquisition method and instrument. This invention also relates to a physiologically-active substance measurement method and instrument. More specifically, the present invention is concerned with a biological information acquisition method and instrument for acquiring information on a living body on the basis of a quantified value of a physiologically active substance collected from a body surface of the living body.

2. Description of the Related Art

Known methods in the past for acquiring information on a stress, emotion, menstrual cycle or the like in a living body (hereinafter called "information on a living body" or "biological information") include biological information acquisition methods based on psychological assessments by diagnostic questions, organoleptic questionnaires or the like, physiological tests based on brain waves, myoelectric potentials or the like, behavior measurements by work performance or the like, and so on. For example, Japanese Patent Laid-open No. 2006-94969 discloses a technology for determining a menstrual cycle on the basis of a heart rate. Further, Japanese Patent No. 2582957 discloses a daily activity level monitoring system for monitoring variations in body temperature or heart rates.

In recent years, technologies have been developed, as simpler methods, to acquire information on a living body by using as an indicator a physiologically active substance contained in blood, urine or saliva. For example, Japanese Patent Laid-open No. Hei 11-38004 discloses a quantification method of a stress, which uses as an indicator the concentration of an adrenal cortical steroid and/or its metabolite contained in saliva. In addition, Japanese Patent Laid-open No. 2000-131318 discloses a method for figuring out a stress in terms of both comfort and discomfort by using as an indicator β-endorphin, dopamine, immunoglobulin A, prostaglandin $D_2$ or the like contained in blood or the like.

SUMMARY OF THE INVENTION

Compared with the methods which rely upon psychological assessments, physiological tests, behavior measurements or the like, the biological information acquisition methods making use of physiologically active substances contained in blood, urine or saliva as indicators are advantageous in that they are simpler and easier and do not demand large systems or instruments.

With these methods, however, blood drawing or work to collect urine or saliva is essential for the quantification of a physiologically active substance. When blood is used, for example, a problem hence arises in that a subject experiences a mental or physical load from blood drawing. In addition, this mental or physical load resulted from the blood drawing may become a stress to cause a variation in the stress, emotion or the like in the subject, leading a potential problem that accurate biological information may not be acquired.

The use of urine or saliva, on the other hand, makes it possible to avoid certain problematic medical action in blood drawing and also to achieve a reduction in the mental or physical load on a subject. However, it is difficult to collect urine or saliva over time or on a constant basis. Moreover, a time lag exists between the collection of urine or saliva and the in vivo metabolism of a physiologically active substance contained in the urine or saliva. There is accordingly a problem in that biological information can hardly be acquired in real time. Although the collection of urine or saliva gives a lower mental or physical load, it makes the subject to become strongly conscious of the collection work, also leading to a potential problem in that accurate biological information may not be acquired.

Therefore, it is desirable to provide a biological information acquisition method, which makes it possible to simply, easily and low invasively collect a physiologically active substance from a living body on a constant basis and also to acquire accurate biological information. It is further desirable to provide a biological information acquisition instrument suitable for practicing such a method. It is still further desirable to provide a physiologically-activate substance measurement method suitable for use in the biological information acquisition method. It is still further desirable to provide a physiologically-activate substance measurement instrument suitable for practicing such a measurement method and suitable for incorporation in the biological information acquisition instrument.

In one embodiment of the present invention, there is thus provided a biological information acquisition method for acquiring information on a living body on a basis of a quantified value of a physiologically active substance originated from the living body, including a procedure of collecting the physiologically active substance from a body surface of the living body.

In the biological information acquisition method, the body surface may be a skin surface of a finger or palm. By collecting the physiologically active substance from the body surface of the living body, the physiologically active substance can be collected simply, easily and low invasively, and moreover, the physiologically active substance can be collected from the living body on a constant basis.

In the biological information acquisition method, the physiologically active substance may be collected from a solvent which has been brought into contact with the body surface.

The physiologically active substance may be a cortisol, and as the information, information on a stress in the living body can be acquired. As an alternative, the physiologically active substance may be a monoamine, and as the information, information on an emotion in the living body can be acquired. As a further alternative, the physiologically active substance may be an estrogen, and as the information, information on a menstrual cycle of the living body can be acquired. As a still further alternative, the physiologically active substance may be growth hormone, and information on effects of exercise in the living body can be acquired.

In another embodiment of the present invention, there is also provided a physiologically-active substance measurement method including collecting from a body surface of a living body a physiologically active substance originated from the living body and quantifying the physiologically active substance.

The physiologically active substance may be at least one physiologically active substance selected from the group consisting of cortisols, monoamines, estrogens and growth hormone.

In a still further embodiment of the present invention, there is also provided a biological information acquisition instrument for acquiring information on a living body on a basis of a quantified value of a physiologically active substance originated from the living body, including a sampling unit for being operatively brought into contact with a body surface of the living body to collect the physiologically active substance from the body surface.

The biological information acquisition instrument may preferably further include a solvent feeder for feeding a solvent to the sampling unit, the sampling unit being provided with an opening for bringing the solvent, which has been fed by the solvent feeder, into contact with the body surface. Preferably, the biological information acquisition instrument may further include an aspirator for applying a negative pressure to the body surface, the opening being provided therearound with a recess such that the body surface, which has been drawn by the aspirator, comes into close contact with the recess to cover and close the recess.

In the biological information acquisition instrument, the sampling unit may include a first member defining therein a first flow passage to permit feeding of the solvent therethrough; a second member inserted in the first member for sliding contact with the first member and defining a second flow passage therein, the second member being arranged movably relative to the first member in a direction of the insertion of the second member to operatively bring the second flow passage into communication with the first flow passage such that a communicated state in which the first flow passage and the second passage are in communication with each other and a non-communication state in which the first flow passage and the second passage are out of communication with each other can be changed over from one to the other; and the opening bored in an upper surface portion of the first member such that the opening can be brought into communication with the second flow passage in the non-communicated state.

In a yet further embodiment of the present invention, there is also provided a physiologically-active substance measurement instrument including a sampling unit for being operatively brought into contact with a body surface of a living body to collect from the body surface a physiologically active substance originated from the living body.

The expression "information on a living body" as used herein includes, in addition to information on a stress, emotion, menstrual cycle, effects of exercise, or the like, for example, drowsiness (alertness level), health conditions, a circadian rhythm (biorhythm), and so on. The term "emotion" as used herein encompasses an excitement, fear, anger, aggression, pleasure, anxiety, and the like.

Further, the expression "physiologically active substance originated from a living body" broadly embraces substances, which exist in a living body, have physiological effects or pharmacological effects on the living body, and therefore, take part in variations in a stress, emotion, menstrual cycle, metabolism or the like in the living body. Specific examples include steroid hormones such as cortisol and estradiol, catecholamines such as adrenaline and dopamine, physiologically active peptides such as oxytocin and endorphin, and the like (see "Table 1" to be described subsequently herein).

According to the biological information acquisition method and instrument of the present embodiment, a physiologically active substance can be simply, easily and low invasively collected from a living body on a constant basis.

DETAILED DESCRIPTION OF THE PREFERRED EMBODIMENTS

Figure 1A:
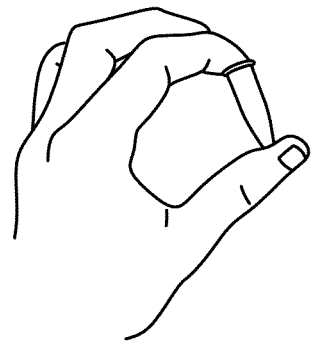
FIGS. 1A and 1B are schematic diagrams illustrating a procedure for collecting a physiologically active substance from a skin surface of a finger.

With reference to the accompanying drawings, a description will hereinafter be made about preferred embodiments for practicing the present invention. It is to be noted that the embodiments to be described hereinafter illustrate some examples of representative embodiments of the present invention and the scope of the present invention shall not be narrowly interpreted by the embodiments. The description will be made in the following order:
<Biological information acquisition method>
1. Brief summary
2. Biological information and biologically active substances
3. Collection and measurements of biologically active substances
<Biological information acquisition instrument>
1. Construction outline of the biological information acquisition instrument
2. Specific construction of the sampling unit
(1) First Embodiment
(2) Second Embodiment
(3) Third Embodiment
(4) Fourth Embodiment
(5) Fifth Embodiment
3. Specific construction of quantification unit
4. Specific construction of analysis unit and output unit
<Biological Information Acquisition Method>
1. Brief Summary With a view to sensing biological information with good accuracy, the present inventors have conducted enthusiastic investigations about sampling methods of biologically active substances from living bodies. As a result, it has been found for the first time that, as will be described in detail in Examples, such biologically active substances can be collected from body surfaces such as fingers, palms, etc.

Concerning physiologically active substances, in the past, it has been the common technical knowledge to collect them from blood, urine, saliva or the like. To the best knowledge of the inventors, no report has heretofore been made about successful collection of a physiologically active substance from a body surface of a living body.

As to the mechanism of collection of a physiologically active substance from a body surface of a living body, its details have not been elucidated. Presumably, however, a physiologically active substance secreted, for example, into sweat or sebum may exist on a body surface. As an alternative possibility, a physiologically active substance in blood may permeate through cells in a body surface and may exist on the body surface. As many of physiologically active substances have solubility in fat and permeability through cell membranes, there is presumably a high possibility that a physiologically active substance existing on a body surface as a result of its secretion into sebum or its permeation through cell membranes can be collected.

An embodiment of the present invention has been completed based on such novel findings as described above, and provides a biological information acquisition method for acquiring information on a living body on the basis of a quantified value of a physiologically active substance originated from the living body, which includes a procedure of collecting the physiologically active substance from a body surface of the living body, and also a biological information acquisition instrument suitable for practicing the method.

According to this biological information acquisition method, biological information can be more simply and easily and less invasively acquired than the existing method that uses as an indicator a physiologically active substance contained in blood, urine or saliva. Owing to the collection of the physiologically active substance existing on the body surface as opposed to blood, urine, saliva or the like, the physiologically active substance can be collected without making the subject become strongly conscious of the sampling work. According to the biological information acquisition method, accurate information can be acquired without inducing a change in a stress, emotion or the like in the subject.

According to this biological information acquisition method, the physiologically active substance secreted or permeated onto the body surface is collected, thereby making it possible to collect the physiologically active substance over a time or on a constant basis. By using as an indicator the physiologically active substance secreted or permeated onto the body surface, the time of collection of the physiologically active substance and the time of in vivo metabolism of the physiologically active substance can be brought into coincidence with each other. According to the biological information acquisition method of an embodiment of the present invention, it is possible to acquire biological information on a subject over a time or on a constant basis and to sense it in real time.

2. Biological Information and Biologically Active Substances

Biological information which can be acquired in an embodiment of the present invention can include, in addition to information on a stress, emotion, menstrual cycle, effects of exercise or the like, for example, drowsiness (alertness level), health conditions, a circadian rhythm (biorhythm), and so on.

With regard to a stress out of these, the existence of a correlation is well known between the loading dose of the stress on the living body and the secretion amounts of cortisol, corticosterone and cortisone (which will hereinafter be collectively called "cortisols") (see Japanese Patent Laid-open No. Hei 11-38004 and Japanese Patent Laid-open No. 2000-131318). It is to be noted that the term "secretion amount" is used herein as a synonym to an amount of excretion into blood, i.e., "blood concentration."

Concerning emotions such as an excitement, fear, anger, aggression, pleasure, anxiety, sorrow and the like, their correlations with norepinephrine, epinephrine, dopamine, and L-dopa as their precursor (which will hereinafter be collectively called "catecholamines") are known. Further, with respect to the secretion amount of serotonin classified as a monoamine like catecholamines, its correlation with an emotion has also been ascertained.

It has been reported that, when a psychosocial test was conducted such that a subject was caused to feel, for example, an anxiety or fear, the saliva noradrenaline level varied after the test (see "Study of salivary catecholamines using fully automated column-switching high-performance liquid chromatography," Journal of Chromatography, B. Biomedical Sciences and Applications, 694(2), 305-16 (Jul. 4, 1997)).

As is also known well, esteron (E1), estradiol (E2) and estriol (E3) (which will hereinafter be collectively called "estrogens") control the menstrual cycle of a living body, and their secretion amounts vary in correlation with the menstrual cycle.

It is also known that the secretion of growth hormone is stimulated by doing effective exercise. The secretion of growth hormone promotes the growth of muscles and bones and promotes the mobilization of body fat to increase the fat burning efficiency. Therefore, effects of muscle enhancement or exercise such as slimming exercise are considered to correlate to the secretion of growth hormone.

Based on a quantified value of cortisol or the like, for example, it is thus possible to obtain information on a stress in a living body. Described specifically, measurements are made to determine, for example, the amounts of cortisol or the like secreted from many normal subjects, and from the results of the measurements, a standard change curve that specifies a standard range of variations in the concentration of cortisol or the like is calculated. The amount of cortisol or the like secreted from a subject is then measured, and is compared with the standard change curve. When the amount of cortisol or the like secreted from the subject is found to depart from the standard change curve as a result of the comparison, for example, the subject can be determined to have a chronic stress.

Further, a measurement is made to determine, for example, the amount of cortisol or the like from a subject during a normal time, and from the results of the measurement, a standard change curve is calculated. By comparing the amount of cortisol or the like, which is secreted at a given time point, with the standard change curve, the level of stress or the level of relax in the subject at that time point can be determined.

As combinations of physiologically active substances as indicators, other than cortisols, monoamines, estrogens and growth hormone, and biological information, the combinations shown in Table 1 are known. The biological information acquisition method according to an embodiment of the present invention can adopt these combinations, and based on positive or negative correlations of biological information with quantified values of the physiologically active substances, information on the living body can be acquired.

TABLE 1

| Biological information | Physiologically active substances | |
|---|---|---|
| Stress | Steroid hormones | Cortisol, corticosterone, cortisone |
| | Peptide | Neuropeptide Y (NPY) |
| Emotion (aggression) | Steroid hormones | Testosterone, dihydrotestosterone(DHT), dehydroepiandrosterone (DHEA), dehydroepiandrosterone sulfate (DHEAS) |
| Emotion (excitement, fear, anger or the like) | Catecholamines | Noradrenaline (norepinephrine), adrenaline (epinephrine), L-dopa |
| Emotion (pleasure) | Catecholamines | Dopamine |
| | Peptide | Endorphin |
| Emotion (anxiety) | Monoamine | Serotonin |
| | Peptide | Oxytocin, vasopressin, galanin |
| Drowsiness (alertness level) | | Melatonin |
| Menstrual cycle | Steroid hormones | Esteron(E1), estradiol(E2), estriol(E3) |

It is to be noted that the physiologically active substances shown in Table 1 are merely illustrative. In addition, catecholamines, for example, metanephrine, normetanephrine, 3-methoxy-4-hydroxymandelic acid, 3-methoxy-4-hydroxyphenylglycol, 3,4-dihydroxymandelic acid, 3,4-dihydroxyphenylglycol, 3,4-dihydroxyphenylacetic acid, 3-methoxytyramine, homovanillic acid, 5-hydroxyindoleacetic acid, vanillylmandelic acid and the like are usable as indicators of biological information. Further, steroid hormones, for example, aldosterone, deoxycorticosterone, androstendione, progesterone, 11-deoxycorticosterone, pregnenolone, 11-deoxycortisol, 17-hydroxyprogesterone, 17-hydroxypregnenolone, cholecalciferol (vitamin D) and the like are also usable as indicators of biological information.

The followings can also be mentioned as physiologically active substances usable as indicators of biological information: As hypophysis hormones, corticotropin releasing hormone (CRH), growth hormone releasing hormone (GRH), somatostatin (growth hormone secretion inhibiting hormone), gonadotropin releasing hormone (GnRH), prolactin releasing hormone (PRH), prolactin inhibiting hormone (PIH), thyrotropin releasing hormone (TRH), thyrotropin (TSH), etc. As thyroid hormones, thyroxine, triiodothyroxine, etc. Various hormones and neurotransmitters such as chromogranin A, adenocorticotropic hormone (ACTH), luteinizing hormone (LH), insulin-like growth factor (IGF-1), prolactin, proopiomelanocortin (POMC), oxytocin, α-melanophore stimulating hormone (α-MSH), glucagon, ghrelin, galanin, motilin, leptin, gastrin, cholecystokinin, selectin, activin, inhibin, neurotensin, bombesin, substance P, angiotensins I and II, enkephalin, orexins A and B, anandamide, acetylcholine, histamine, glutamic acid, glycine, aspartic acid, pyrimidine, adenosine, adenosine triphosphate (ATP), GABA (gamma-aminobutyric acid), FMRFamide, peptide YY, agouti-related peptide (AGRP), cocaine- and amphetamine-regulated transcript (CART) peptide, calcitonin gene related peptide (CGRP), glucagons-like peptides 1,2 (GLP-1,2), vasoactive intestinal peptide (VIP), gastrin releasing peptide (GRP), melanin concentrating hormone (MCH), etc.

It is also to be noted that correlations between these physiologically active substance and biological information are not limited to those shown in Table 1. For example, serotonin can be used as indicators of dementia praecox and agrypnia in addition to emotion, and estrogens can also be used as indicators of infertility, climacteric symptom, manic-depressive state in addition to the menstrual cycle. In addition, an embodiment of the present invention can also be applied to all the combinations of physiologically active substances and their corresponding biological information, said combinations having been ascertained to date.

3. Physiologically-Active Substance Measurement Method

A description will next be made about a procedure for collecting a physiologically active substance from a body surface and measuring the same, that is, the physiologically-active substance measurement method according to an embodiment of the present invention.

The physiologically active substance, which exists on the body surface as a result of its secretion or permeation, can be collected in a solvent, for example, by bringing the solvent into contact with the body surface. Usable solvents can be water and various organic solvents. For example, ethanol-water can be used. No particular limitation is imposed on the body surface with which the solvent is brought into contact, but a skin surface of a finger, palm or the like is convenient.

As a suitable specific example of the procedure for collecting the physiologically active substance from the body surface, procedures for collecting the physiologically active substance from a skin surface of a finger will be described with reference to FIGS. 1A and 1B, respectively.

FIG. 1A illustrates the procedure for collecting the physiologically active substance from a skin surface of a forefinger by using a microtube.

A top opening of the microtube, in which a solvent such as ethanol-water is contained, is brought into contact with the finger tip of the forefinger, and the microtube is supported at a lower end thereof by the thumb. With the microtube being held in place between the forefinger and the thumb, the microtube is turned upside down to bring the solvent into contact with the skin surface of the forefinger. As a consequence, the physiologically active substance which exists on the skin surface of the forefinger can be collected in the solvent contained inside the microtube.

Figure 1B:

FIG. 1B illustrates the procedure for collecting the physiologically active substance from a skin surface of a forefinger by using a syringe.

A solvent such as ethanol-water is filled in a distal end portion of the syringe. With the syringe being maintained in contact with the forefinger, the syringe is held by the thumb and the middle finger. A piston of the syringe is drawn by the right hand to develop a negative pressure within the syringe. As a consequence, the syringe is stuck on the skin surface, and the solvent was allowed to remain in contact with the skin surface of the forefinger for one minute. According to this procedure, the solvent which has been maintained in contact with the skin surface can be recovered with a higher yield based on the negative pressure in the syringe in comparison with the collection by the microtube shown in FIG. 1A.

With reference to FIGS. 1A and 1B, the descriptions have been made of the procedures for collecting the physiologically active substance in the solvent maintained in direct contact with the body surface. The collection of a physiologically active substance in a solvent can also be conducted as will be described hereinafter. For example, a plastic plate or the like is firstly pressed against a body surface to have the physiologically active substance, which exists on the body surface, adhered to a surface of the plastic plate or the like. The solvent is then dropped onto the surface of the plastic plate or the like, and the physiologically active substance so adhered is dissolved and collected in the solvent.

In some instances, it is not absolutely necessary to use a solvent for the collection of a physiologically active substance from a body surface. Firstly, the physiologically active substance is caused to adhere to a surface of a solid. Subsequently, by blowing nitrogen gas or the like against the surface of the solid or by ultrasonically oscillating or heating the solid, the physiologically active substance so adhered is released and then collected with a gas or the like.

The quantification of the physiologically active substance can be performed by using a known method such as, for example, high-performance liquid chromatography (HPLC), enzyme immunoassay or radioimmunoassay. As will be mentioned in detail in the next description of "the biological information acquisition instrument," the quantification can also be conducted by a surface plasmon sensor (SPR), a quartz crystal microbalance sensor (QCM) or the like.

According to the above-described physiologically-active substance measurement method, a physiologically active substance can be simply, easily and low invasively quantified by collecting the physiologically active substance from a body surface such as a finger or palm. This method can, therefore, be utilized to conduct the diagnosis, prevention or prognostic observation of various diseases by determining the health conditions of living bodies by using physiologically active substances, for example, such as those shown in Table 1. Specifically, the physiologically-active substance measurement method can be utilized, for example, for the prevention or prognostic observation of chronic stress by diagnosing the presence or absence of stress based on the measurement of a cortisol. Further, it is also contemplated, for example, to conduct the diagnosis or the like of the presence or absence of a cartinoid tumor by the measurement of a catecolamine or to conduct the diagnosis or the like of dementia praecox, agrypnia, endogenomorphic depression, damping syndrome or migraine by the measurement of serotonin. Furthermore, the physiologically-active substance measurement method can also be utilized for the diagnosis or the like of an estrogen-dependent disease such as infertility, breast cancer, uterine fibroid or endometriosis, a climacteric symptom or the like by measuring an estrogen or the like.

Further, growth hormone is known to decrease in secretion rate with aging, and is also known to function on the metabolism of carbohydrates, proteins and lipids to take part in the onset of life-style related diseases such as diabetes, hypertension and hyperlipemia. Other growth-hormone-related diseases include those associated with a decrease in the secretion rate of growth hormone, such as growth hormone deficiency (in other words, pituitary dwarfism), hypopituitarism, hypothyroidism, obesity, and chronic renal failure; and those associated with an increase in growth hormone, such as gigantism, hyperpituitarism, ectopic growth hormone producing tumor, and extreme subnutrition such as anorexia syndrome. It is, therefore, possible to perform the determination of an extent of aging, the diagnosis of a life-style related disease or growth-hormone-related disease, or the like by conducting the measurement of growth hormone in accordance with the physiologically-active substance measurement method according to an embodiment of the present invention.

<Biological Information Acquisition Instrument>

A description will next be made of the biological information acquisition instrument according to an embodiment of the present invention. No particular limitation is imposed on this biological information acquisition instrument, insofar as it has a construction that makes it possible to practice the above-described biological information acquisition method. However, preferred embodiments will hereinafter be described.

1. Construction Outline of the Biological Information Acquisition Instrument

Figure 2:
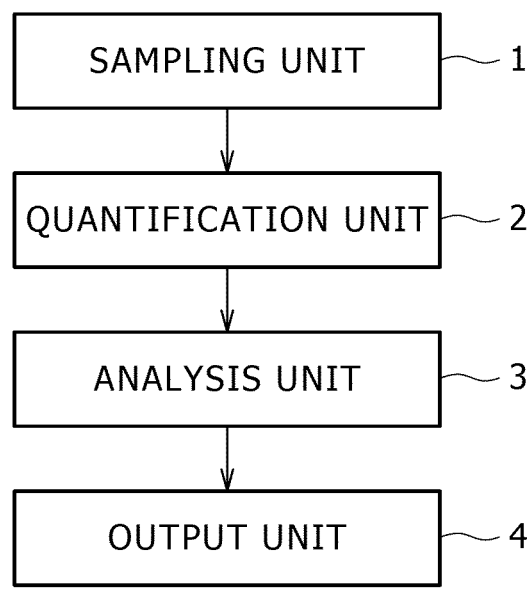
FIG. 2 is a block diagram showing the construction of a biological information acquisition instrument according to the present embodiment.

Referring to FIG. 2, the biological information acquisition instrument according to the present invention will hereinafter be described. The biological information acquisition instrument is provided with a sampling unit 1, which is brought into contact with a body surface to collect a physiologically active substance from the body surface. FIG. 2 also shows a quantification unit 2 for quantifying the physiologically active substance collected by the sampling unit 1, an analysis unit 3 for acquiring biological information on the basis of the quantified value, and an output unit 4 for outputting the results of a determination of the biological information. It is to be noted that the physiologically-active substance measurement instrument according to an embodiment of the present invention can be constructed from the sampling unit 1, quantification unit 2 and output unit 4 and the analysis unit 3 is not an essential element.

2. Specific Construction of the Sampling Unit

FIG. 3, FIGS. 4A and 4B, FIGS. 5A and 5B, FIGS. 7A through 8C and FIGS. 9A through 12C depict sampling units 1A,1B,1C,1D,1E according to the first, second, third, fourth and fifth embodiments, respectively. The sampling units 1A,1B,1C,1D,1E have openings 11A,11B,11C,111,211, respectively, with which a body surface S as a fingertip (see FIGS. 3 through 5B) is brought into contact. Further, the sampling units 1A,1B,1C,1D,1E also have solvent feeders (designated at numeral 5 in FIGS. 3, 4A, 4B, 5A and 5B) for feeding a solvent to the body surface S maintained in contact with the respective openings 11A,11B,11C,111,211.

(1) First Embodiment

Figure 3:
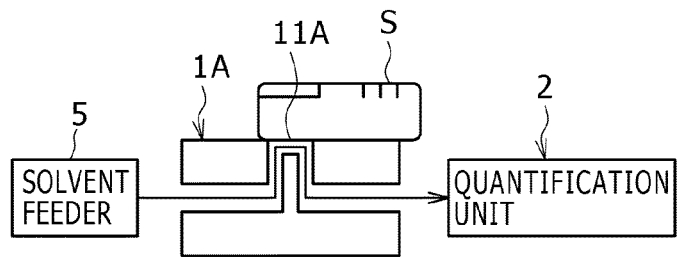
FIG. 3 is a schematic diagram depicting the construction of a sampling unit according to a first embodiment.

Referring to FIG. 3, the construction of the first embodiment (i.e., the sampling unit 1A) of the sampling unit 1 will be specifically described. In FIG. 3, the arrow indicates a feed direction of the solvent by the solvent feeder 5. The solvent is fed rightwards as viewed in the diagram, and subsequent to contact with the body surface S in the opening 11A, is fed to the quantification unit 2. As a result, a physiologically active substance existing on the body surface S is collected in the solvent, and is provided for a measurement at the quantification unit 2. According to this construction, the quantification of the physiologically active substance can be performed on a constant basis by continuously feeding the physiologically active substance from the body surfaces to the quantification unit 2. It is to be noted that the solvent feeder 5 can be a commonly-employed pump or the like.

(2) Second Embodiment

Figure 4A:
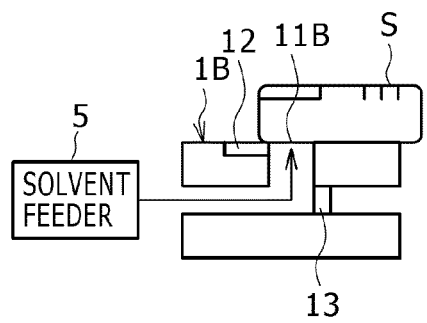
FIGS. 4A and 4B are schematic diagrams depicting the construction of a sampling unit according to a second embodiment.
Figure 4B:
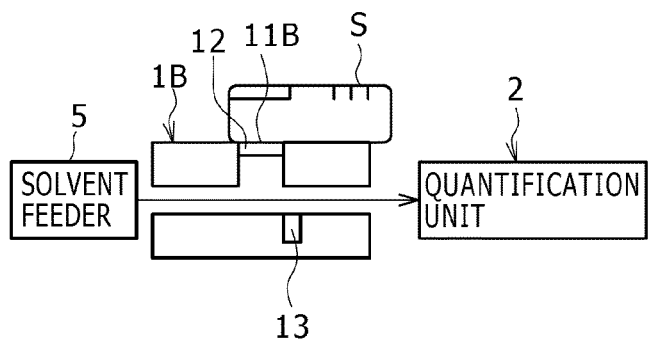

The sampling unit 1 can also be constructed as the sampling unit 1B of the construction depicted in FIGS. 4A and 4B. In FIGS. 4A and 4B, numerals 12 and 13 indicate on/off valves, respectively. In FIG. 4A, the valve 12 arranged in the opening 11B is open, while the valve 13 arranged in a communication part to the quantification unit 2 is closed. In this state, the solvent fed by the solvent feeder 5 as shown by the arrow in the diagram is in a state that it is in contact with the body surface S which is in turn maintained in contact with the opening 11B. To prevent the solvent from leaking out through the opening 11B in the above-described state, it is desired to construct the sampling unit 1B such that the feeding of the solvent by the solvent feeder 5 is stopped when the feed pressure of the solvent exceeds a predetermined pressure.

Reference is next had to FIG. 4B. The valve 12 arranged in the opening 11B is closed, while the valve 13 arranged in the communication part to the quantification unit 2 is opened. As a result, the solvent which has been in contact with the body surface S in the opening 11B is fed to the quantification unit 2. By repeating the opening and closure of the valves 12,13, the physiologically active substance can be intermittently collected from the body surface S and fed to the quantification unit 2.

(3) Third Embodiment

With reference to FIG. 3 and FIGS. 4A and 4B, the descriptions have been made of the constructions in each of which the solvent is brought into direct contact with the body surface in the sampling unit 1A or 1B to collect the physiologically active substance in the solvent. The sampling unit 1 can also be constructed as the sampling unit 1C as will be described hereinafter. Described specifically, in the sampling unit 1C depicted in FIGS. 5A and 5B, a contact plate 14 is arranged turnably upside down in the opening 11C.

Figure 5A:
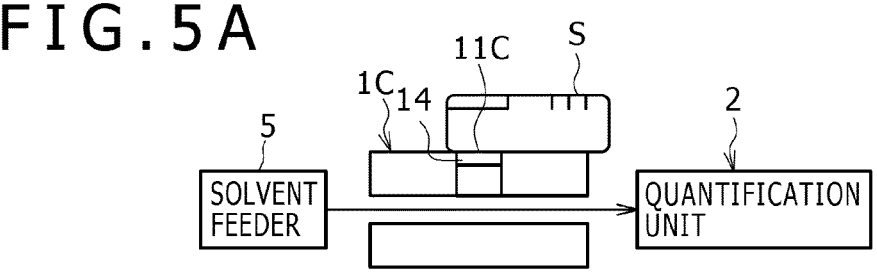
FIGS. 5A and 5B are schematic diagrams depicting the construction of a sampling unit according to a third embodiment.
Figure 5B:
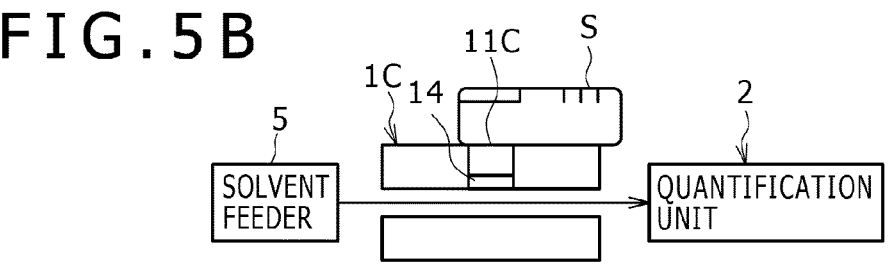

When the body surface S is pressed against the contact plate 14 as depicted in FIG. 5A, the physiologically active substance existing on the body surface S adheres to a surface of the contact plate 14. When the contact plate 14 is then caused to turn upside down as depicted in FIG. 5B, the physiologically active substance adhered on the surface of the contact plate 14 is dissolved in the solvent fed by the solvent feeder and is fed to the quantification unit 2. By repeatedly causing the contact plate 14 to turn upside down, it is thus possible to intermittently collect the physiologically active substance from the body surfaces and to feed it to the quantification unit 2.

Figure 6A:
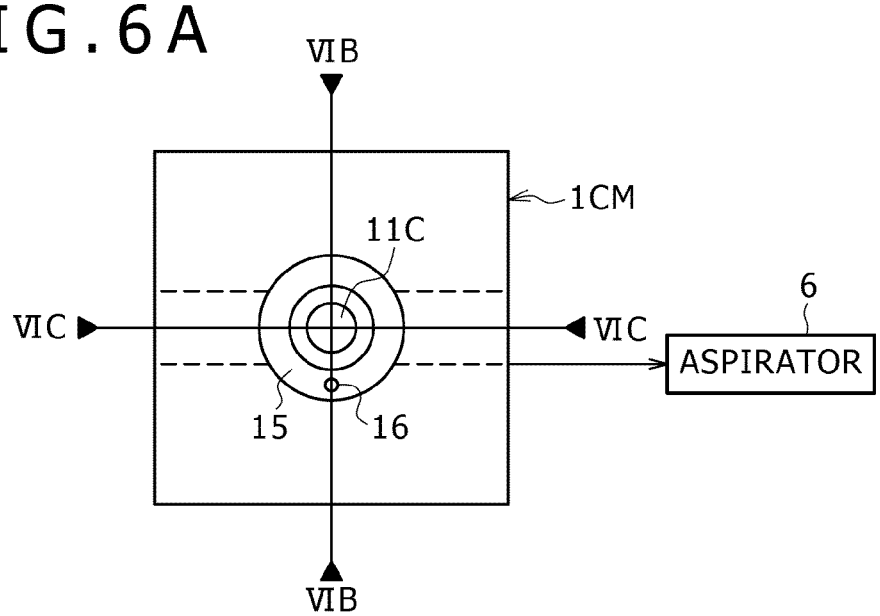
FIG. 6A is a schematic, transparent, plan view depicting the construction of a sampling unit according to a modification of the third embodiment shown in FIGS. 5A and 5B, and FIGS. 6B and 6C are schematic cross-sectional views of the sampling unit of FIG. 6A.
Figure 6B:
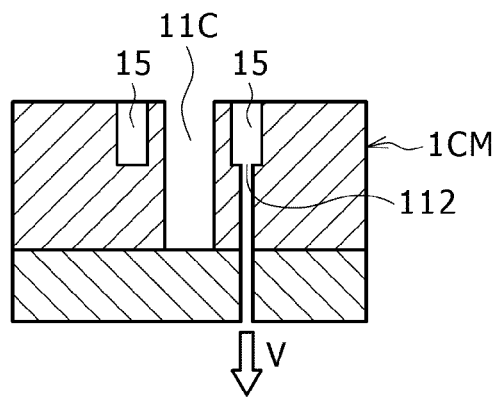
Figure 6C:
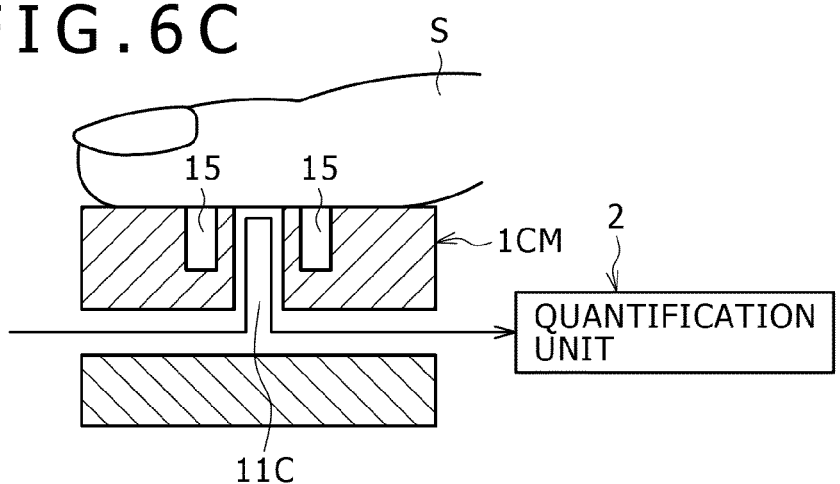

For the prevention of leakage of the solvent from the opening 11C, a recess may preferably be arranged surrounding, in other words, around the opening 11C of the sampling unit 1C such that the body surface S is drawn into close contact with the opening 11C. FIG. 6A is a schematic, transparent, plan view depicting, as a modification of the third embodiment, a sampling unit 1CM with a recess 15 arranged around the opening 11C, and FIGS. 6B and 6C are schematic cross-sectional views taken along lines VIB-VIB and VIC-VIC, respectively, of FIG. 6A.

The recess 15 is formed as a groove in the form of a circle surrounding the opening 11C as viewed from the top (see FIG. 6A). An exhaust orifice 16 connected to an aspirator 6 is bored though a bottom of the recess 15 at a location thereof. The aspirator 6 draws air from the inside of the recess 15 through the exhaust orifice 16 and exhausts it (see an arrow V in FIG. 6B), thereby applying a negative pressure to the body surface S maintained in contact with the sampling unit 1CM. Under this negative pressure, the body surface S is brought into close contact with the sampling unit 1CM so that the recess 15 is closed air-tight (see FIG. 6C). As a consequence, the body surface S also comes into close contact with the opening 11C located centrally of the recess 15 and hence, hermetically closes the opening 11C. It is, accordingly, possible to effectively prevent leakage of the solvent from the opening 11C. For the enhancement of the close contact with the body surface S, elastic members of rubber or silicone may be arranged on parts of the recess 15 and opening 11C, which come into contact with the body surface S. For such elastic members, however, it is necessary to use a material which is free from the dissolution of its component or components into the solvent and does not affect the measurement of a physiologically active substance at the quantification unit 2. The aspirator 6 can be a vacuum pump or the like employed in the past. Such a vacuum pump may preferably be one capable of measuring a negative pressure applied to the body surface S and detecting any leakage of the solvent.

(4) Fourth Embodiment

Figure 7A:
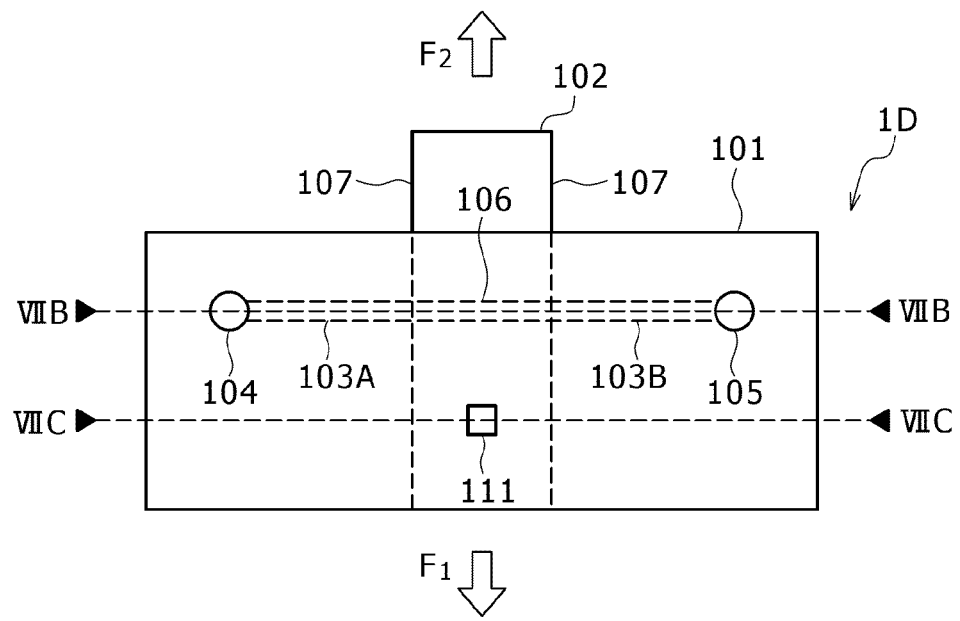
FIG. 7A is a schematic, transparent, plan view depicting the construction of a sampling unit according to a fourth embodiment in a communicated state.
Figure 7B:
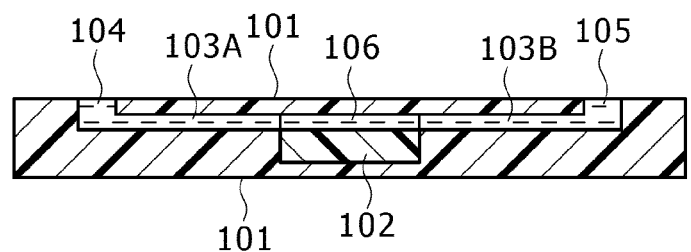
FIGS. 7B and 7C are schematic cross-sectional views depicting the construction of the sampling unit of the fourth embodiment in the communicated state.
Figure 7C:
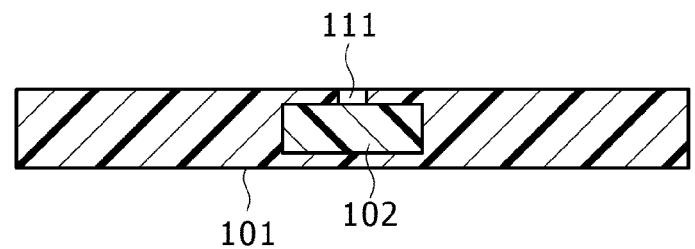

With reference to FIGS. 7A through 7C and FIGS. 8A through 8C, the construction of the sampling unit 1D according to the fourth embodiment will hereinafter be described. FIG. 7A is a schematic, transparent, plan view, and FIGS. 7B and 7C are schematic cross-sectional views taken along lines VIIB-VIIB and VIIC-VIIC, respectively, of FIG. 7A.

In FIG. 7A, the sampling unit designated at sign 1D is composed of a first member 101 and a second member 102. The first member 101 defines first flow passages 103A,103B through which a fluid can be fed. The second member 102 is inserted for sliding contact in the first member 101, and defines a second flow passage 106 which can be brought into communication with the first flow passages 103A,103B. In FIGS. 7A and 7C, numeral 111 indicates an opening bored in an upper surface portion of the first member 101.

In the sampling unit 1D, the first member 101 and the second member 102 are arranged such that the second member 102 is movable relative to the first member 101 in the direction of the insertion of the second member 102 (see the block arrows $F_1$ and $F_2$ in FIG. 7A). As a consequence, a communicated state, in which the first flow passages 103A, 103B and the second flow passage 106 are in communication with each other as depicted in FIGS. 7A through 7C, and a non-communicated state, in which the first flow passages 103A,103B and the second flow passage 106 are out of communication with each other as depicted in FIGS. 8A through 8C, can be changed over from one to the other by moving the second member 102 relative to the first member 101.

In the communicated state depicted in FIGS. 7A through 7C, the first flow passages 103A,103B formed in the first member 101 and the second flow passage 106 formed in the second member 102 are communicated together to form a single flow passage. FIGS. 7A and 7B illustrate a fluid inlet 104 to the first flow passage 103A and a fluid outlet 105 from the first fluid passage 103B to the quantification unit 2. To the fluid inlet 104, an unillustrated fluid feeder is connected. On the other hand, the fluid outlet 105 is connected to the quantification unit 2. In this communicated state, the solvent introduced from the fluid inlet 104 into the first flow passage 103A is fed to the second flow passage 106, and is then fed from the first flow passage 103B to the quantification unit 2 via the fluid outlet 105.

Figure 8A:
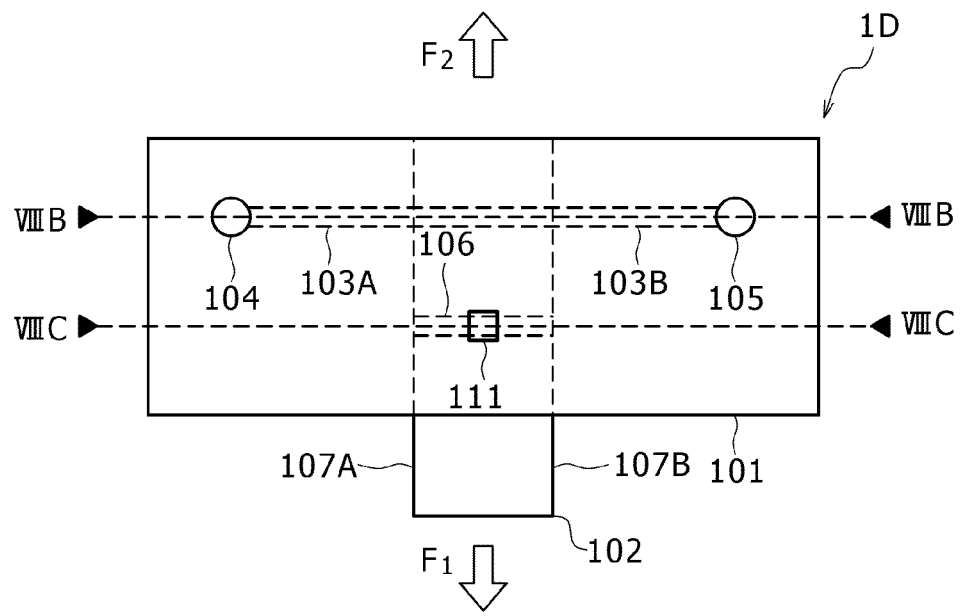
FIG. 8A is a schematic, transparent, plan view depicting the construction of the sampling unit of the fourth embodiment in a non-communicated state.
Figure 8B:
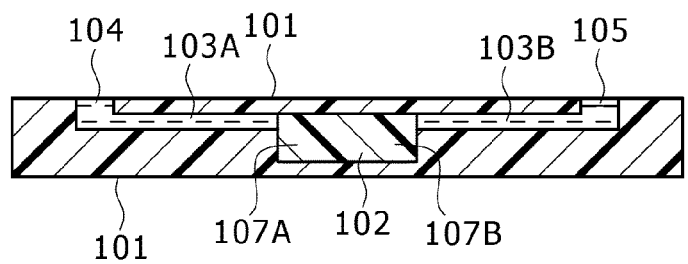
FIGS. 8B and 8C are schematic cross-sectional views depicting the construction of the sampling unit of the fourth embodiment in the non-communicated state.
Figure 8C:
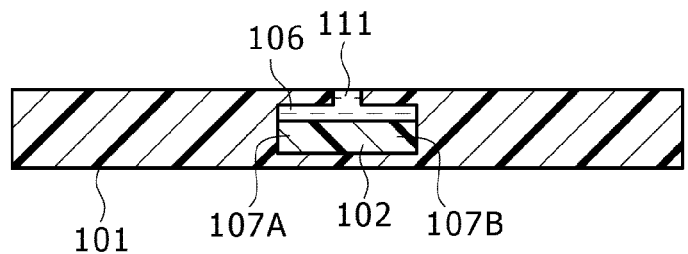

When the second member 102 is moved in the direction $F_1$ of its insertion relative to the first member 101 in the sampling unit 1D which is in the communicated state, the communicated state of the first flow passages 103A,103B and the second flow passage 106 is cancelled to assume the non-communicated state as depicted in FIGS. 8A through 8C.

In the non-communicated state depicted in FIGS. 8A through 8C, the flow of the solvent introduced from the fluid inlet 104 into the first flow passage 103A is blocked up by one 107A of slide contact walls 107A,107B of the second member 102, said one slide contact wall 107A being located on the side of the first flow passage 103A (see FIG. 8B). At this time, in the second flow passage 106 of the second member 102 moved in the direction $F_1$ of its insertion, the solvent which has flowed in the communicated state is held in such a form that the flow of the solvent is cut off by slide contact walls of the first member 101, said slide contact walls being associated with the slide contact walls 107A,107B (see FIG. 8C).

An opening 111 bored in an upper surface portion of the first member 101 can be brought into communication with the second flow passage 106 in the non-communicated state. Described specifically, when the second member 102 is moved in the direction $F_1$ of its insertion relative to the first member 101 and the second flow passage 106 is moved to a position corresponding to the opening 111, the second flow passage 106 is communicated to the outside via the opening 111. As a consequence, the solvent held in the second flow passage 106 is exposed to the outside through the opening 111.

When the body surface S is brought into contact with the opening 111 in this state as depicted in FIG. 3, etc., the solvent held in the second flow passage 106 comes into contact with the body surface S so that a physiologically active substance existing on the body surface S is collected in the solvent.

After the body surface S is maintained in contact with the opening 111 for a predetermined time to sufficiently collect the physiologically active substance in the solvent held in the second flow passage 106, the second member 102 is moved in the direction $F_2$ of its insertion relative to the first member 101 to assume the communicated state depicted in FIG. 7A again. As a consequence, by the solvent introduced from the fluid inlet 104 into the first flow passage 103A, the solvent held in the second flow passage 106 and containing the physiologically active substance is fed to the quantification unit 2 via the first flow passage 103B.

As has been described above, the movements of the second member 102 relative to the first member 101 in the sampling unit 1D make it possible to perform the step of causing the predetermined amount of the solvent to flow into the second flow passage 106 in the communicated state, the step of collecting the physiologically active substance in the solvent held in the second flow passage 106 in the non-communicated state, and the step of establishing the communicated state again to feed the solvent, which is held in the second flow passage 106 and contains the physiologically active substance, to the quantification unit 2.

According to the sampling unit 1D, the physiologically active substance can be intermittently collected from the body surface S and measured through simple operations by repeating these steps. The repetition of the individual steps can be effected by automatically controlling the relative movement of the first member 101 and the second member 102.

(5) Fifth Embodiment

Figure 9A:
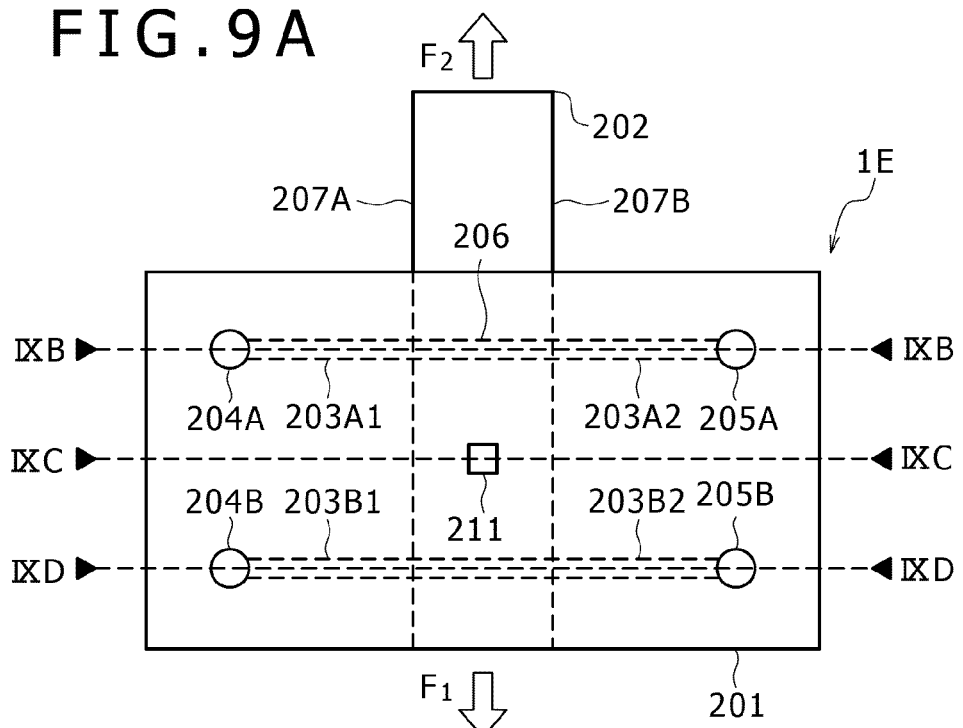
FIG. 9A is a schematic, transparent, plan view depicting the construction of a sampling unit according to a fifth embodiment in a communicated state.
Figure 9B:
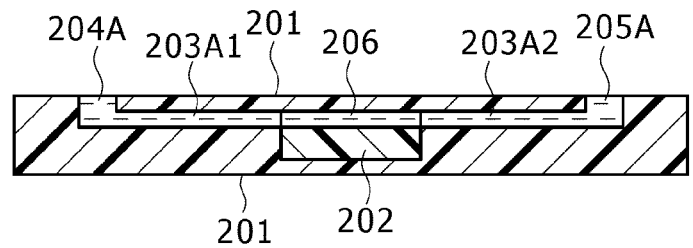
FIGS. 9B through 9D are schematic cross-sectional views depicting the construction of the sampling unit of the fifth embodiment in the communicated state.
Figure 9C:
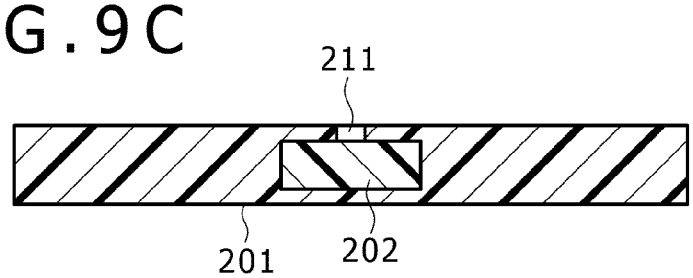
Figure 9D:
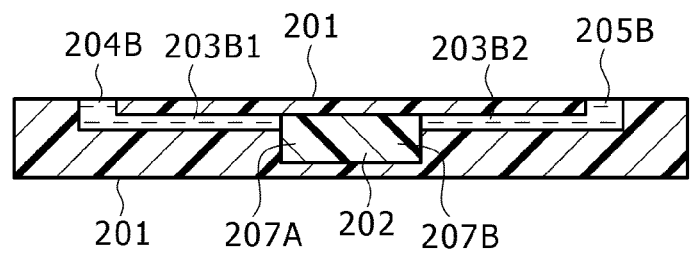
Figure 10A:
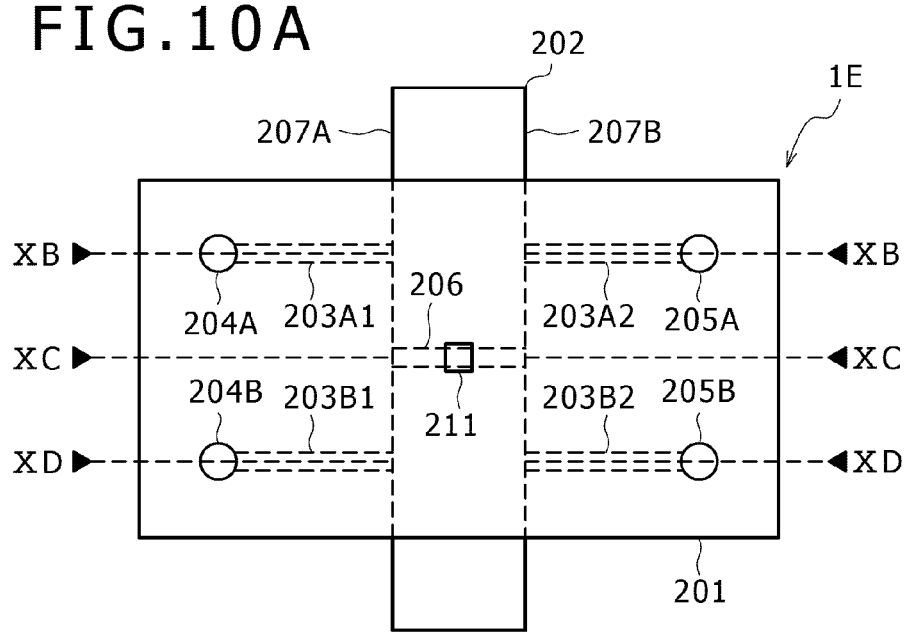
FIG. 10A is a schematic, transparent, plan view depicting the construction of the sampling unit according to the fifth embodiment in a non-communicated state.
Figure 10B:
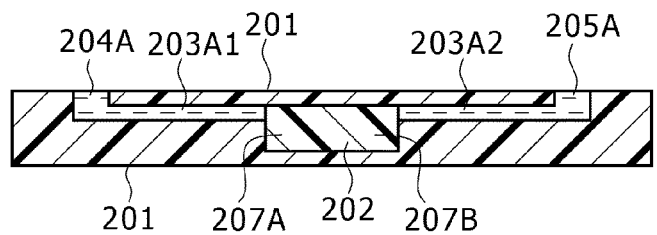
FIGS. 10B through 10D are schematic cross-sectional views depicting the construction of the sampling unit of the fifth embodiment in the non-communicated state.
Figure 10C:
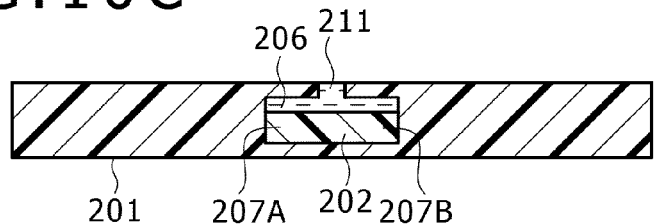
Figure 10D:
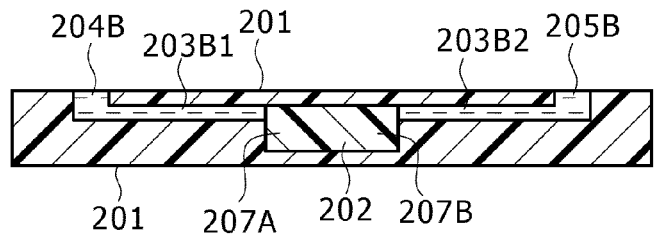
Figure 11A:
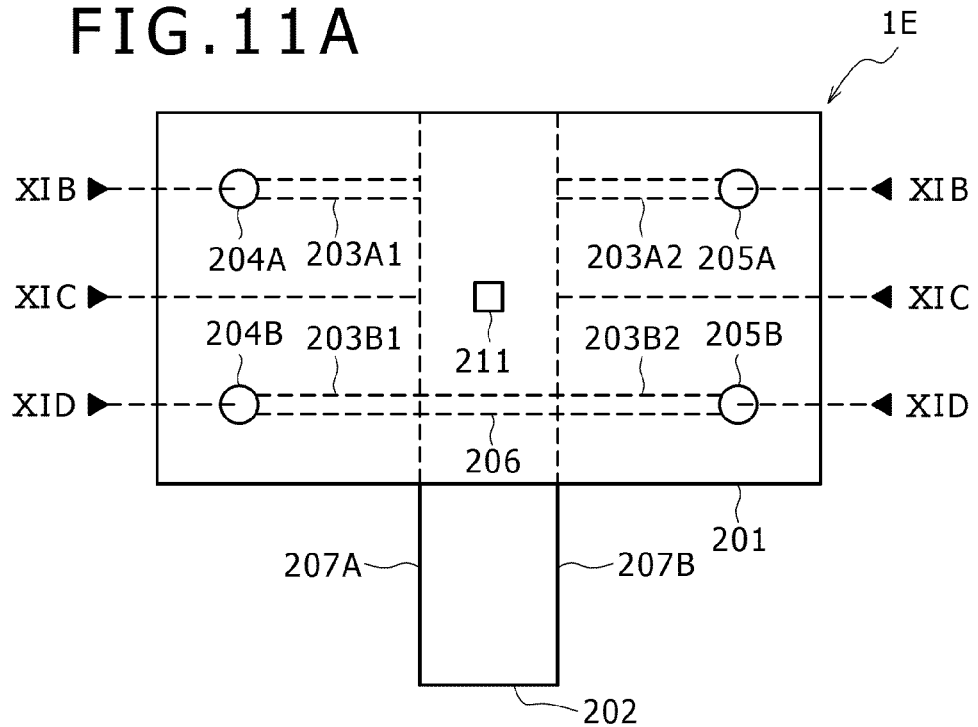
FIG. 11A is a schematic, transparent, plan view depicting the construction of the sampling unit according to the fifth embodiment in a re-communicated state.
Figure 11B:
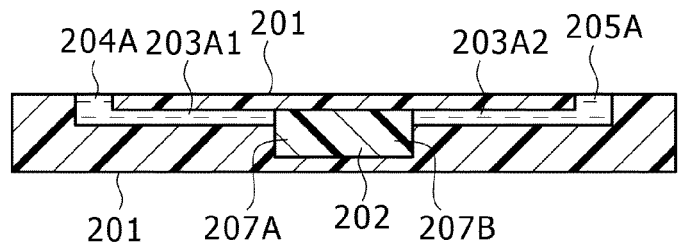
FIGS. 11B through 11D are schematic cross-sectional views depicting the construction of the sampling unit of the fifth embodiment in the re-communicated state.
Figure 11C:
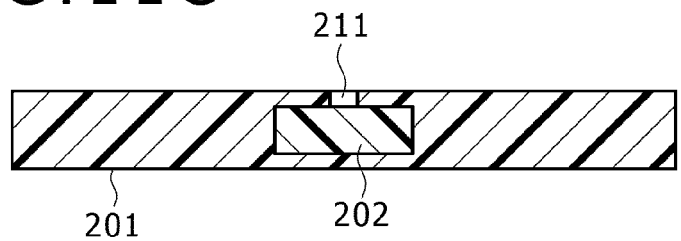
Figure 11D:
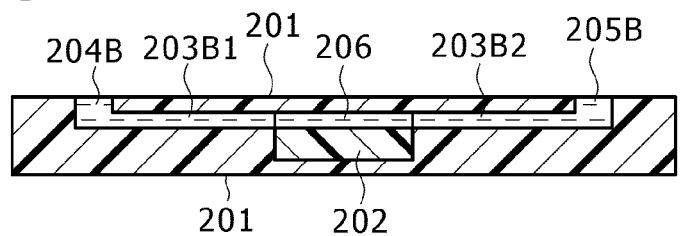

With reference to FIGS. 9A through 9D, FIGS. 10A through 10D and FIGS. 11A through 11D, the construction of the sampling unit 1E according to the fifth embodiment will hereinafter be described. FIGS. 9A, 10A and 11A are schematic, transparent, plan views. FIGS. 9B, 9C and 9D are schematic cross-sectional views taken along lines IXB-IXB, IXC-IXC and IXD-IXD of FIG. 9A, respectively. FIGS. 10B, 10C and 10D are schematic cross-sectional views taken along lines XB-XB, XC-XC and XD-XD of FIG. 10A, respectively. FIGS. 11B, 11C and 11D are schematic cross-sectional views taken along lines XIB-XIB, XIC-XIC and XID-XID of FIG. 11A, respectively.

In FIGS. 9A through 11D, the sampling unit designated at sign 1E is different from the above-mentioned sampling unit 1D in that in a first member 201, two sets of first flow passages 203A1,203A2 and first flow passages 203B1,B2 are arranged in parallel to each other. The sampling unit 1E is also different from the sampling unit 1D in that the opening 211 is bored between the two sets of first flow passages as viewed in the direction of the insertion of a second member 202 (see the block arrows $F_1$ and $F_2$ in FIG. 9A).

The sampling unit 1E is composed of the first member 201 and the second member 202. The first member 201 defines the first flow passages 203A1,203A2 and second flow passages 203B1,203B2, through which a fluid can be fed. The second member 202 is inserted for sliding contact in the first member 201, and defines a second flow passage 206 which can be brought into communication with one of the first flow passages 203A1,203A2 and second flow passages 203B1, 203B2.

By moving the second member 202 in the direction of its insertion (see the block arrows $F_1$ and $F_2$ in FIG. 9A) relative to the first member 201, the sampling unit 1E can be changed over among a communicated state, a non-communicated state and a re-communicated state. In the communicated state, the first flow passages 203A1,203A2 and the second flow passage 206 are in communication with each other as depicted in FIGS. 9A through 9D. In the non-communicated state, neither the first flow passages 203A1,203A2 nor the first flow passages 203B1,203B2 are in communication with the second flow passage 206 as depicted in FIGS. 10A through 10D. In the re-communicated state, the first flow passages 203B1, 203B2 and the second flow passage 206 are in communication with each other as depicted in FIGS. 11A through 11D.

In the communicated state depicted in FIGS. 9A through 9D, the first flow passages 203A1,203A2 formed in the first member 201 and the second flow passage 206 formed in the second member 202 are communicated together to form a single flow passage. FIGS. 9A, 9B and 9D illustrate a fluid inlet 204A to the first flow passage 203A1 and a fluid outlet 205A from the first fluid passage 203A2. To the fluid inlet 204A, an unillustrated fluid feeder is connected. In this communicated state, the solvent introduced from the fluid inlet 204A into the first flow passage 203A1 is fed to the second flow passage 206, and is then discharged from the first flow passage 203A2 to the outside of the instrument via the fluid outlet 205A.

When the second member 202 is moved in the direction $F_1$ of its insertion relative to the first member 201 in the sampling unit 1E which is in the communicated state, the communicated state of the first flow passages 203A1,203A2 and the second flow passage 206 is cancelled to assume the non-communicated state as depicted in FIGS. 10A through 10D.

In the non-communicated state depicted in FIGS. 10A through 10D, the flow of the solvent introduced from the fluid inlet 204A into the first flow passage 203A1 is blocked up by one 207A of slide contact walls 207A,207B of the second member 202, said one slide contact wall 207A being located on the side of the first flow passage 203A1 (see FIG. 10B). At this time, in the second flow passage 206 of the second member 202 moved in the direction $F_1$ of its insertion, the solvent which has flowed in the communicated state is held in such a form that the flow of the solvent is cut off by slide contact walls of the first member 201, said slide contact walls being associated with the slide contact walls 207A,207B (see FIG. 10C).

The opening 211 bored in an upper surface portion of the first member 201 can be brought into communication with the second flow passage 206 in the non-communicated state. When the second member 202 is moved in the direction $F_1$ of its insertion relative to the first member 201 and the second flow passage 206 is moved to a position corresponding to the opening 211, the second flow passage 206 is communicated to the outside via the opening 211. As a consequence, the solvent held in the second flow passage 206 is exposed to the outside through the opening 211.

When the body surface S is brought into contact with the opening 211 in this state as depicted in FIG. 3, etc., the solvent held in the second flow passage 206 comes into contact with the body surface S so that a physiologically active substance existing on the body surface S is collected in the solvent.

After the body surface S is maintained in contact with the opening 211 for a predetermined time to sufficiently collect the physiologically active substance in the solvent held in the second flow passage 206, the second member 202 is moved further in the direction $F_1$ of its insertion relative to the first member 201. As a result, the sampling unit 1E assumes the re-communicated state in which the second flow passage 206 and the first flow passages 203B1,203B2 are in communication with each other as depicted in FIGS. 11A through 11D.

To the fluid inlet 204B, an unillustrated fluid feeder is connected. On the other hand, the quantification unit 2 is connected to the fluid outlet 205B. In this re-communicated state, by the solvent introduced from the fluid inlet 204B into the first flow passage 203B1, the solvent held in the second flow passage 206 and containing the physiologically active substance is fed to the quantification unit 2 via the first flow passage 203B2.

It is to be noted that the solvent, which is to be fed to the fluid inlet 204B by the fluid feeder, can be a solvent useful for the collection of the physiologically active substance like the solvent fed from the fluid inlet 204A. Instead of the solvent useful for the collection of the physiologically active substance, the solvent to be fed to the fluid inlet 204B can also be a solvent which contains an appropriate solvent (an equilibrated buffer or the like) or a reagent needed for the measurement (an antibody or the like) depending upon, for example, HPLC, SPR or QCM adopted as the quantification unit 2.

Further, gas (air or the like) may be introduced as a fluid from the fluid inlet 204B into the first flow passage 203B1. By the gas so introduced, the solution which is held in the second flow passage 206 and contains the physiologically active substance can be fed to the quantification unit 2 without dilution.

Figure 12A:
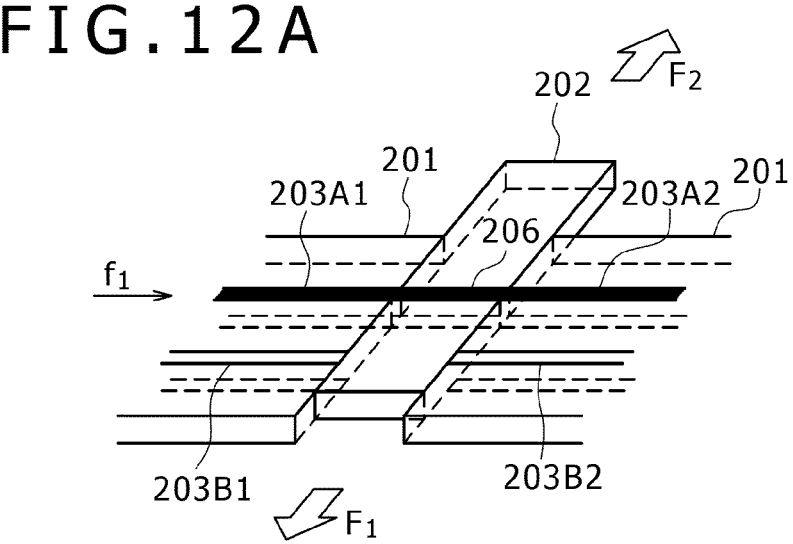
FIGS. 12A through 12C are fragmentary, perspective, transparent views depicting operations of the sampling unit of the fifth embodiment in the communicated state, non-communicated state and re-communicated state, respectively.

Based on FIGS. 12A through 12C, a specific description will be made about an embodiment that introduces gas into the first flow passage 203B1 via the fluid inlet 204B. As illustrated in FIG. 12A, in the communicated state of the first flow passages 203A1,203A2 and the second flow passage 206 (also see FIGS. 9A and 9B), the solvent is firstly fed in the direction of the arrow $f_1$ in FIG. 12A so that the solvent is flowing through the second flow passage 206.

Figure 12B:
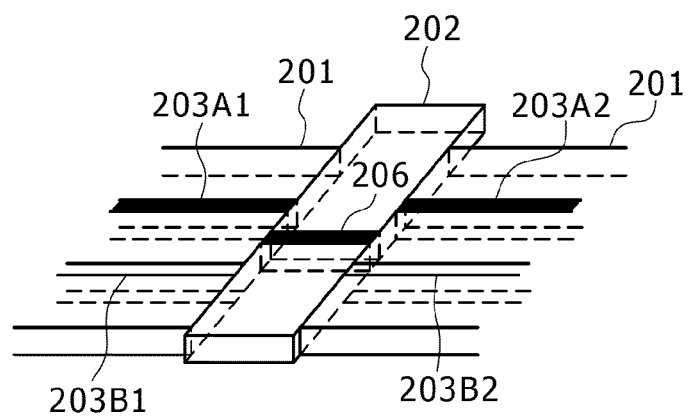

When the second flow passage 206 is next brought into the non-communicated state with the first flow passages 203A1, 203A2 as depicted in FIG. 12B (also see FIGS. 10A, 10B and 10C), the flow of the solvent is cut off by the slide contact walls of the first member 201, said slide contact walls being associated with the above-described slide contact walls 207A,207B. As a result, a predetermined amount of the solvent is held in the second flow passage 206. This predetermined amount is equal to the volume of the second flow passage 206, which is defined by its cross-sectional area x its length. By bringing the body surface S into contact with the predetermined amount of the solvent, which is held in the second flow passage 206, via the opening 211 as described above, the physiologically active substance is collected in the solvent.

Figure 12C:
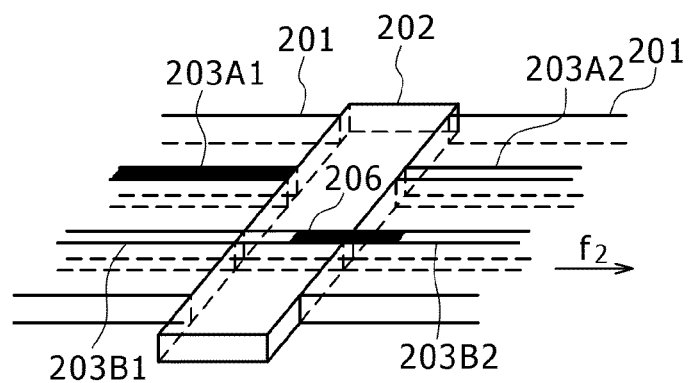

As illustrated in FIG. 12C, the second flow passage 206 is then brought into communication with the first flow passage 203B1,203B2, and the gas is introduced into the first flow passage 203B1. As a result, the solvent which is held in the second passage 206 and contains the physiologically active substance is fed to the quantification unit 2 via the first flow passage 203B2 by the thus-introduced gas. The solvent which is held in the second passage 206 and contains the physiologically active substance can, therefore, be fed in the same amount to the quantification unit 2 without dilution. As a result, the quantification of the physiologically active substance at the quantification unit 2 can be performed with high sensitivity, and moreover, an accurate quantification can be performed while maintaining the volume of the sample constant.

The above-mentioned sampling units 1D,1E can be constructed as so-called microchips. As the material of the first members 101,201 and second members 102,202, a glass material such as silica or borosilicate glass, a silicone rubber such as polydimethylsiloxane (PDMS), an acrylic resin such as polymethyl methacrylate (PMMA), or the like is usable. The formation of the flow passages arranged in the respective members may be conducted by wet etching or dry etching of glass-made substrate layers or nanoimprinting, injection molding or machining of plastic substrate layers. These descriptions equally apply to the sampling units 1A,1B,1C.

3. Specific Construction of the Quantification Unit

The quantification unit 2 can comprise a high-performance liquid chromatograph (HPLC), surface plasmon sensor (SPR), a quartz crystal microbalance sensor (QCM), or the like, and performs the quantification of the physiologically active substance collected by the sampling unit 1. The quantification unit 2 can also be constructed to perform the measurement of the physiologically active substance on the basis of a known method such as enzyme immunoassay or radioimmunoassay. It is, however, desired to adopt HPLC, SPR or QCM for the quantification unit 2, because HPLC, SPR or QCM can omit a labeling step needed for enzyme immunoassay or radioimmunoassay, and therefore, can simplify the construction of the quantification unit 2.

From the viewpoint of the accuracy of a measurement, the adoption of SPR or QCM is more desired. With HPLC, the physiologically active substance is detected as a peak on a chromatogram so that the accuracy of its measurement may be lowered if a signal ascribable to an impurity or a noise enters the peak intensity. With SPR or QCM, on the other hand, the physiologically active substance is detected by an antibody immobilized on a surface of a sensor, and therefore, a high measurement accuracy can be obtained based on the specificity of the antibody. In addition, SPR and QCM have an advantage that they are higher in throughput than HPLC and can make the quantification unit 2 smaller.

A description will hereinafter be made by taking, as an example, a case in which the quantification unit 2 comprises SPR.

In SPR, an antibody to a detection target substance is immobilized on a surface of a sensor, and the amount of the detection target substance bound to the antibody is quantified by an SPR angle shift. However, many of physiologically active substances develop only small changes in dielectric constant so that SPR angle shifts can hardly be detected. SPR may, therefore, have difficulty in performing a quantification with good accuracy in some instances. It is, accordingly, desired to adopt so-called indirect competitive SPR for the quantification unit 2.

According to indirect competitive SPR, a physiologically active substance is firstly immobilized on a surface of a sensor. A sample, which contains the physiologically active substance as a quantification target, and a predetermined amount of an antibody to the physiologically active substance are then mixed, and the resulting reaction mixture is fed to the sensor. The antibody competitively binds to the physiologically active substance in the reaction mixture and also to the physiologically active substance immobilized on the surface of the sensor. When the antibody has bound to the physiologically active substance immobilized on the surface of the sensor, an SPR angle shift takes place. In indirect competitive SPR, the more the physiologically active substance contained in the sample, the smaller the amount of the antibody to be bound to the physiologically active substance immobilized on the surface of the sensor, and therefore, the smaller the resulting SPR angle shift. Conversely, the smaller the physiologically active substance contained in the sample, the greater the resulting SPR angle shift. Based on the SPR angle shift resulting from this binding of the antibody, it is possible to quantify the physiologically active substance even if usual SRP cannot perform its quantification. By appropriately changing the amount of the antibody to be mixed with the sample, the dynamic range of the measurement can be controlled as desired.

The immobilization of the physiologically active substance on the surface of the sensor can be conducted by a method which is employed in common. For example, a biotinylated, physiologically active substance is immobilized onto an avidin-coated sensor by using the avidin-biotin reaction. Further, a physiologically active substance can also be immobilized by aminating an end of a linker which extends from a functional group of the physiologically active substance, applying a carboxylic acid modification to a sensor, and making use of an amide linkage between an amino group and a carboxyl group. Furthermore, it is also possible to directly bind the physiologically active substance to a noble metal surface by thiolating (—SH) the end of the linker and making use of a linkage between the noble metal and a thiol group. In addition, a specific protein can be bound to the end of the linker, and the physiologically active substance can then be physically adsorbed on a surface which permits ready adsorption of proteins, such as a surface of gold or a surface of hydrophobic plastics or an inorganic material.

It is to be noted that the functional group to be added to the linker, the chain length of the linker, the immobilization density and the like need to be set under such conditions as maintaining the antigenicity of the physiologically active substance to the antibody.

4. Specific Construction of the Analysis Unit and Output Unit

The analysis unit 3 and output unit 4 can be constructed by an analysis processor unit and display unit employed in general HPLC, SPR or QCM. At the analysis unit 3, the acquisition of biological information is performed by using, as an indicator, a value quantified by the quantification unit 2. Described specifically by way of example, the amounts of a physiologically active substance in many normal subjects over a predetermined time range in a day are measured, and from the measurement results, a standard change curve that specifies a standard range of changes in the concentration of the physiologically active substance is calculated. The amounts of the physiologically active substance in a subject are then compared with the standard change curve to determine biological information. The thus-obtained determination results are outputted to the output unit 4, and are displayed on a screen or the like.

EXAMPLES

Example 1

Quantification of Cortisol

1. Collection of Cortisol from Skin Surface

With respect to each of six subjects, cortisol was collected from the skin surface of a finger three times (10:00, 14:00, 18:00) a day by the following two procedures.

(1) Collection by Microtube

The fingertip of the forefinger was lightly wiped with ethanol-moistened paper towel. A microtube in which 1:1 ethanol-water (50 µL) was contained was brought into contact at an upper opening thereof with the fingertip of the forefinger, and the microtube was supported at a lower end thereof by the thumb (see FIG. 1A). With the microtube being held by the forefinger and the thumb, the microtube was turned upside down and the 1:1 ethanol-water was maintained in contact with the skin surface of the forefinger for 1 minute. It is to be noted that the initial wiping of the fingertip with the paper towel was intended to remove cortisol beforehand in view of the possible accumulation of cortisol on the skin surface in addition to the removal of impurities existing on the skin surface.

(2) Collection by Syringe

The fingertip of the forefinger was lightly wiped with ethanol-moistened paper towel. In a distal end portion of a syringe, 1:1 ethanol-water (50 µL) was filled. With the syringe being maintained in contact with the fingertip of the forefinger, the syringe was held by the thumb and the middle finger (see FIG. 1B). A piston of the syringe was drawn by the right hand to develop a negative pressure within the syringe. As a consequence, the syringe was stuck on the skin surface, and the 1:1 ethanol-water was maintained in contact with the skin surface of the forefinger for 1 minute. According to this procedure, the 1:1 ethanol-water which had been maintained in contact with the skin surface was recovered with a higher yield based on the negative pressure in the syringe in comparison with the collection by the microtube described above under (1).

2. Quantification of Cortisol by High-Performance Liquid Chromatography (HPLC)

The 1:1 ethanol-water which had been brought into contact with the skin surface (hereinafter simply called "the sample") (40 µL) was recovered in a vial. An aliquot (30 µL) of the sample was provided for an analysis which employed a high-performance liquid chromatograph ("NANOSPACE SI-2," trade name; manufactured by Shiseido Co., Ltd.).

Using "CAPCELL PAK MF Ph-1" (column size: 1.5 mm ID×35 mm, column temperature: 35° C.; trade name, product of Shiseido Co., Ltd.) as a pretreatment column, 2.5:1 acetonitrile-water was fed at a flow rate of 100 µL/min. As an analysis column, on the other hand, "CAPCELL PAK C18 UG120" (column size: 1.5 mm ID×250 mm, column temperature: 35° C.; trade name, product of Shiseido Co., Ltd.) was used, and 10 mM phosphate buffer (pH 6.8)/$CH_3N$ (78/22) was fed at a flow rate of 100 µL/min. A detection was performed by an UV absorbance detector (wavelength: 242 nm UV). The measurement time was set for 50 min.

Firstly, standard-brand cortisol (product of Wako Pure Chemical Industries, Ltd.) was prepared as a 0.5 uM cortisol/cortisone aqueous solution, and a preliminary study was conducted. Confirmed by that preliminary study were the time (from the $2.7^{th}$ to $4.4^{th}$ minutes after the initiation of the measurement) during which the valve was maintained switched toward the analysis column in place of the pretreatment column and the elution time of cortisol (from the $36^{th}$ to $38^{th}$ minutes after the initiation of the measurement).

Figure 13:
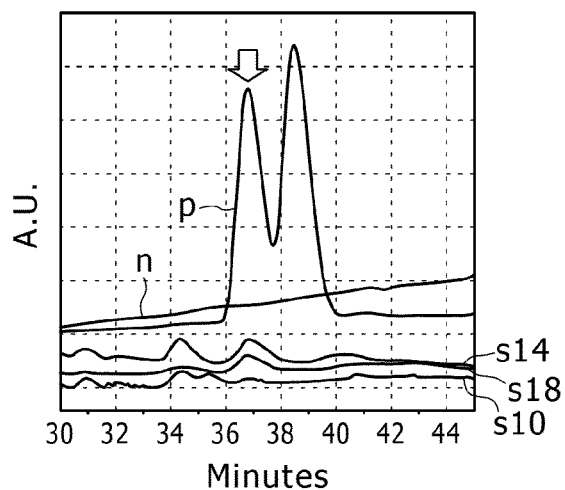
FIG. 13 is a diagram showing the results of quantitative measurements of cortisol by high-performance liquid chromatography (HPLC) with respect to a single subject (Example 1)

FIG. 13 shows the results of the measurements of the amounts of cortisol in samples collected three times (10:00, 14:00, 18:00) a day from a single subject. In the diagram, the samples at the respective hours (see signs s10, s14 and s18) can be confirmed to have cortisol peaks consistent with the corresponding peak of the standard product, which is indicated by sign p (see the block arrow). It is to be noted that in the diagram, sign n indicates the measurement results of 1% ethanol-water which had not been brought into contact with any skin.

Figure 14:
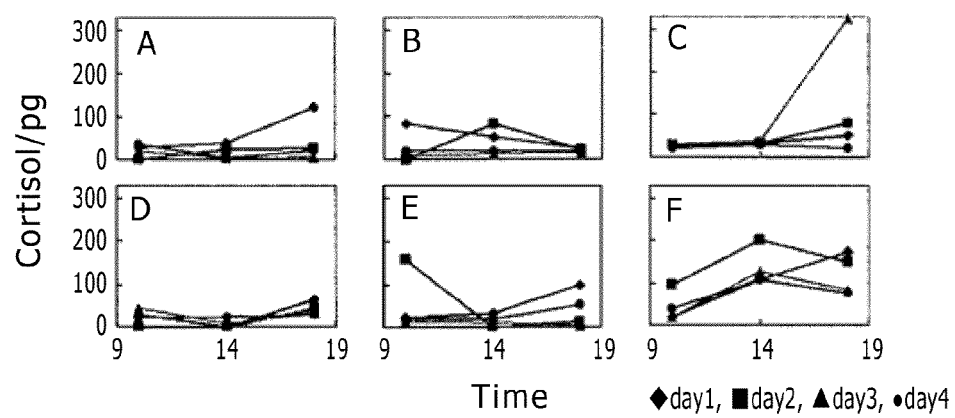
FIG. 14 shows diagrams illustrating the results of quantitative measurements of cortisol by high-performance liquid chromatography (HPLC) with respect to six subjects (Example 1)

With respect to six subjects (subjects A to F), measurements were conducted for 4 days. Based on the results of the measurements, peak areas were calculated relative to a baseline. Using a calibration line, the amounts (pg) of cortisol were determined as shown in FIG. 14. FIG. 14 shows the results of measurements conducted over 4 days with respect to six subjects (subject A to F). It has been confirmed that cortisol can be collected from a skin surface as much as from several picograms in the case of a small amount to 300 pg in the case of a large amount.

3. Quantification of Cortisol by Use of Surface Plasmon Sensor (SPR)

With respect to each sample prepared by the procedure (collection by a syringe) described in Example 1, an analysis was conducted by indirect competitive SPR which employed a surface plasmon sensor ("BIACORE X"; trade name, manufactured by Biacore K.K.). The analysis was conducted following the procedure to be described hereinafter.

(1) Immobilization of Cortisol on the Surface of SPR Sensor

Employed as an SPR sensor was "SA CHIP" (trade name, product Biacore K.K.), on a surface of which streptoavidin had been immobilized beforehand. The standard-brand cortisol was biotinylated. The resulting biotinylated cortisol was dissolved in "Acetate 4.0" (trade name, product Biacore K.K.). The thus-obtained solution (100 µL) was injected at a flow rate of 10 µL/min, and by the avidin-biotin reaction, cortisol was immobilized on the surface of the SPR sensor. Cortisol to be immobilized was set at approx. 150 RU.

(2) Preparation of Calibration Line

Firstly, the standard-brand cortisol which had been formulated into a 10 mM solution in DMSO (dimethyl sulfoxide) was serially diluted with 1:1 ethanol-water to prepare standard solutions containing cortisol at concentrations of 100, 50, 25, 12.5, 6.25, 3.13, 1.56 and 0.78 nM, respectively. The standard solution of each concentration (40 µL) was thoroughly mixed with a 5 ng/mL anti-cortisol antibody solution (40 µL) to conduct a binding reaction. An aliquot (25 µL) of a standard sample solution after the binding reaction was injected at 10 µL/min and 25° C. As the anti-cortisol antibody, a mouse monoclonal antibody ("XM210"; trade name, product of Abcam K.K.) was used, and as a running buffer, "HBS-EP BUFFER" (trade name, product of Biacore K.K.) was used.

Figure 15:
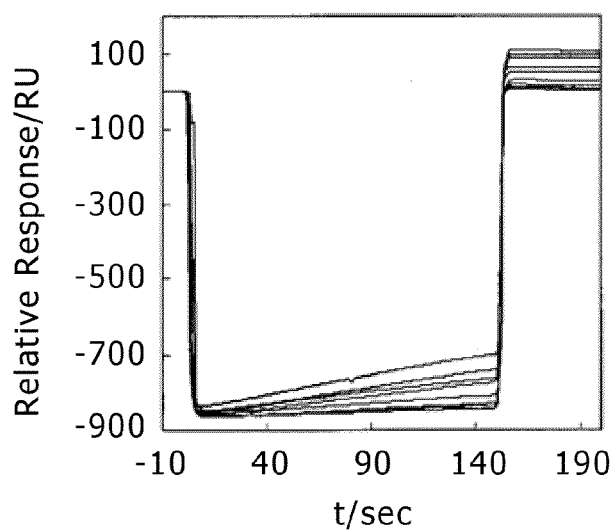
FIG. 15 is a diagram showing an SPR curve obtained with respect to a standard-brand cortisol solution (Example 1)

SPR curves obtained from the cortisol solutions of the respective concentrations are shown in FIG. 15. In the diagram, each peak shift of about 850 RU (Resonance Unit) occurred at 0 sec is attributed to the bulk effect resulted from the switching from the running buffer to the corresponding standard sample solution. This bulk effect disappeared at 150 sec by the switching from the standard sample solution to the running buffer.

From the $0^{th}$ to $150^{th}$ seconds, a time-dependent increase of RU is observed owing to the binding of the anti-cortisol antibody to the cortisol immobilized on the surface of the sensor substrate. It is confirmed that the increment of RU becomes smaller as the standard cortisol solution has a higher concentration but becomes greater as the standard cortisol solution has a lower concentration. This indicates that the measurement principle of indirect competitive SPR is functioning.

Figure 16A:
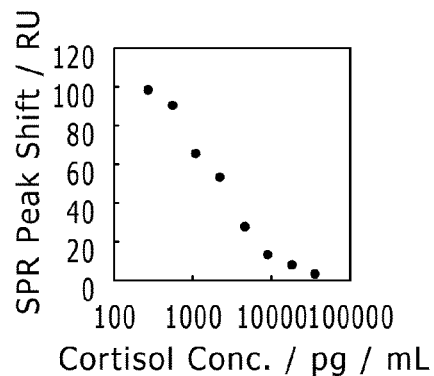
FIGS. 16A and 16B are diagrams depicting plots and a calibration line of SBR shifts, respectively, as obtained with respect to the standard-brand cortisol solution (Example 1)

FIG. 16A shows plots obtained by comparing RUs at the $60^{th}$ sec after the completion of the injection with a baseline.

(3) Measurement of Samples

Figure 16B:
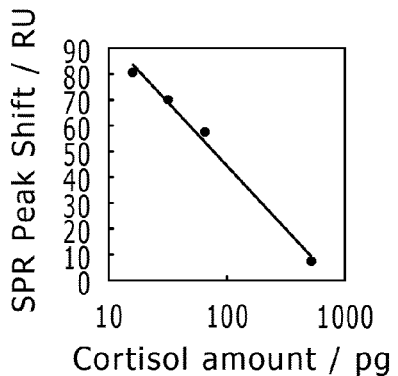

The sample (40 μL) prepared in Example 1 was thoroughly mixed with an aliquot (40 μL) of the anti-cortisol antibody solution to conduct a binding reaction. An aliquot (40 μL) of a standard sample solution after the binding reaction was injected at 20 μL/min and 25° C. A calibration line prepared under similar conditions is shown in FIG. 16B.

The amounts (pg) of cortisol calculated by using the calibration curve with respect to eight subjects (subjects a to h) are shown in Table 2. It was possible to detect cortisol as much as several tens picograms on each of the subjects.

TABLE 2

| Subject | Response/RU | Cortisol/pg |
|---------|-------------|-------------|
| a | 72.5 | 27.10 |
| b | 91.5 | 11.09 |
| c | 53.8 | 65.33 |
| d | 76.4 | 22.56 |
| e | 74.7 | 24.44 |
| f | 68.3 | 33.02 |
| g | 57.2 | 55.67 |
| h | 47.6 | 87.46 |

Example 2

Quantification of Catecholamines

1. Collection of Norepinephrine and L-Dopa from Skin Surface

Following the procedure described under "(1) Collection by microtube" in "1. Collection of cortisol from skin surface" in Example 1, norepinephrine and L-dopa were collected from a skin surface. In this Example, however, water was used as a solvent, and the time of contact with the skin surface was set for 3 minutes.

2. Quantification of Cortisol by High-Performance Chromatography (HPLC)

An aliquot (40 μL) of the water which had been brought into contact with the skin surface (hereinafter simply called "the sample") was recovered in a vial. An aliquot (30 μL) of the sample was provided for an analysis which employed the high-performance liquid chromatograph ("NANOSPACE SI-2", trade name; manufactured by Shiseido Co., Ltd.).

Using "CAPCELL PAK MF Ph-1" (column size: 1.5 mm ID×35 mm, column temperature: 35° C.; trade name, product of Shiseido Co., Ltd.) as a pretreatment column, 2.5:1 acetonitrile-water was fed at a flow rate of 100 μL/min. As an analysis column, on the other hand, "CAPCELL PAK C18 MGII S5" (column size: 2.0 mm ID×250 mm, column temperature: 40° C.; trade name, product of Shiseido Co., Ltd.) was used. Employed as a mobile phase was a 90/10 mixed solvent of (A) and (B) (A: 1.0 mM sodium octanesulfonate, 0.02 mM EDTA-2Na, 10 mM $KH_2PO_4$, 0.05 vol % $H_3PO_4$; (B): $CH_3CN$). The mobile phase was fed at a flow rate of 200 μL/min. The detection was performed by an electrochemical detector ("ECD 0X", trade name; manufactured by Shiseido Co., Ltd.; 800 mV), and the measurement time was set for 30 minutes. The injection volume was set at 2 μL and also at 5 μL.

Figure 17:
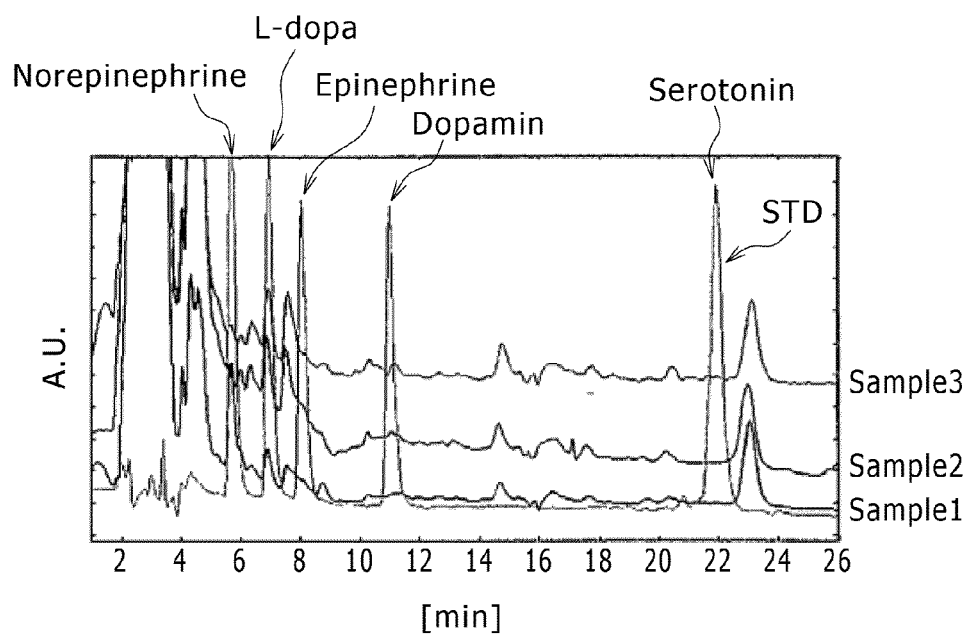
FIG. 17 is a diagram depicting the results of quantitative measurements of norepinephrine and L-dopa by high-performance liquid chromatography (HPLC) (Example 2)

The measurement results are shown in FIG. 17. "Sample 1" indicates a chromatogram obtained from a 6-fold concentrate of the above-described sample, while "Sample 2" and "Sample 3" indicate chromatograms obtained from the sample without concentration. Further, "STD" indicates a chromatogram obtained from a standard-brand solution (a solution containing norepinephrine, epinephrine, L-dopa, dopamine and serotonin).

In the chromatogram of each of Samples 1 to 3, peaks ascribable to norepinephrine and L-dopa were detected. On the other hand, peaks ascribable to epinephrine, dopamine and serotonin were not detected.

Peak areas were calculated relative to a baseline. The amounts (pg) of norepinephrine and L-dopa as calculated by using calibration lines are shown in Table 3.

TABLE 3

| | Injection volume | | | |
|---|---|---|---|---|
| | 2 μL | | 5 μL | |
| | Norepinephrine | L-dopa | Norepinephrine | L-dopa |
| Sample 1 | 7.58 | 2.42 | 19.37 | 7.17 |
| Sample 2 | N.D. | 5.50 | N.D. | 15.68 |
| Sample 3 | N.D. | 5.35 | N.D. | 14.71 |

Norepinephrine was below the detection limit (N.D.) in Sample 2 and Sample 3 which were not subjected to concentration, while its amount was from several to several tens picograms or so in Sample 1 which was subjected to concentration. On the other hand, L-dopa was quantified to be from several to several tens picograms or so in all of Samples 1 to 3. From these results, it has been confirmed that approximately several pg/μL of norepinephrine and L-dopa can be collected from a skin surface.

Example 3

Quantification of Serotonin

1. Collection of Serotonin from Skin Surface

Following a similar procedure as in Example 2, serotonin was collected from a skin surface.

2. Quantification of Serotonin by High-Performance Chromatography (HPLC)

An aliquot (100 μL) of water which had been brought into contact with the skin surface (hereinafter simply called "the sample") was recovered in a vial. The sample (100 μL) was provided for an analysis which employed the high-performance liquid chromatograph ("NANOSPACE SI-2," trade name; manufactured by Shiseido Co., Ltd.).

As a pretreatment column, "CAPCELL PAK C18 MGII S5" (column size: 2.0 mm ID×35 mm, column temperature: 40° C.; trade name, product of Shiseido Co., Ltd.) was used. As an analysis column, on the other hand, "CAPCELL PAK C18 UG120 S3" (column size: 1.5 mm ID×250 mm, column temperature: 40° C.; trade name, product of Shiseido Co., Ltd.) was used. Employed as a mobile phase was a 87/13 mixed solvent of (A) and (B) (A: 4.0 mM sodium octanesulfonate, 0.02 mM EDTA-2Na, 5 mM $KH_2PO_4$ (pH 3.4); (B): $CH_3CN$). The mobile phase was fed at a flow rate of 100 μL/min. The detection was performed by an electrochemical detector ("ECD 0X," trade name; manufactured by Shiseido Co., Ltd.; 750 mV), and the measurement time was set for 40 minutes. The injection volume was set at 1 μL.

Figure 18:
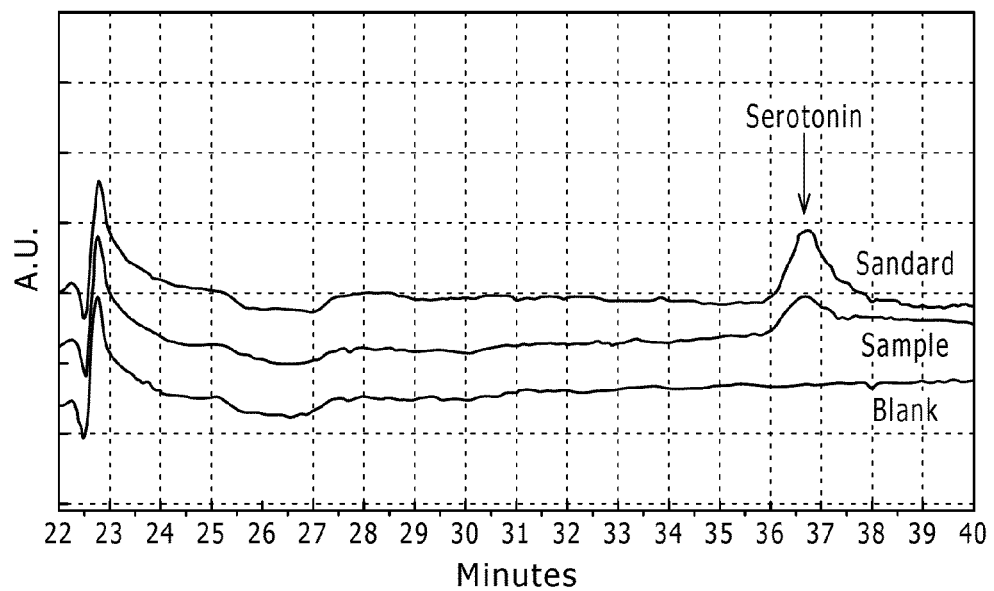
FIG. 18 is a diagram depicting the results of quantitative measurements of serotonin by high-performance liquid chromatography (HPLC) (Example 3)

The measurement results are shown in FIG. 18. "Sample" indicates a chromatogram obtained from a 100-fold concentrate of the above-described sample, while "Standard" designates a chromatogram obtained from a 0.1 µM solution of a standard-brand serotonin (product of Wako Pure Chemical Industries, Ltd.).

In the chromatograms of the sample and standard-brand serotonin, peaks were detected at an elution time of from 36 to 38 minutes, respectively. As a result of a calculation of the serotonin concentrations from the areas in the chromatograms, the serotonin concentration of the 100-fold concentrate of the sample was determined to be approx. 4.4 ng/mL. It was, therefore, possible to collect approx. 0.044 ng/mL of serotonin from the skin surfaces of the forefingers.

Example 4

Quantification of Estradiol

1. Collection of Estradiol from Skin Surface

Following a similar procedure as in Example 2, serotonin was collected from a skin surface. The collection of estradiol was conducted from eight subjects.

2. Quantification of Estradiol by Enzyme-Linked Immunosorbent Assay (ELIZA)

An aliquot (100 µL) of water which had been brought into contact with the skin surface (hereinafter simply called "the sample") was recovered in a vial. The sample (100 µL) was provided for an analysis which employed a commercial ELISA kit ("HIGH SENSITIVITY SALIVARY 17β-ESTRADIOL IMMUNOASSAY KIT", trade name; product of Salimetrics, LLC).

Figure 19:
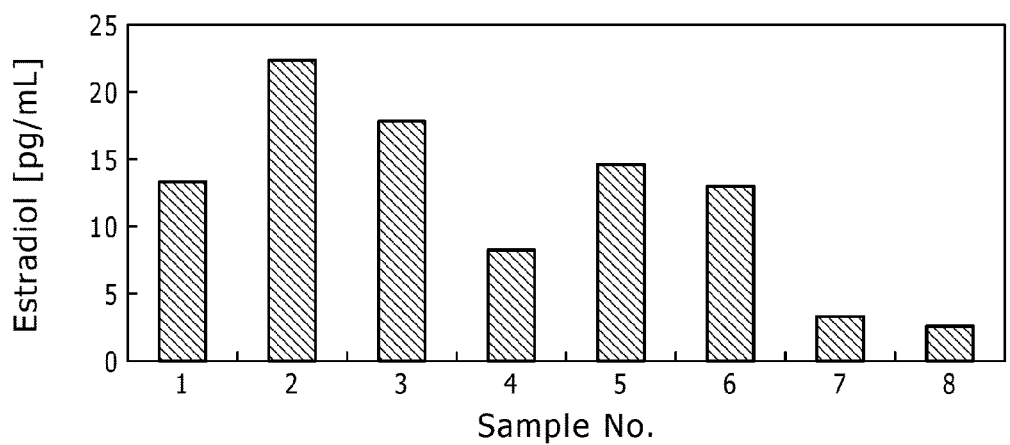
FIG. 19 is a diagram depicting the results of quantitative measurements of estradiol by enzyme immunoassay (ELISA) (Example 4)

By measuring the standard-brand estradiol enclosed in the kit, a calibration line was prepared. Using the calibration curve, the concentrations of estradiol in the samples were calculated. The calculation results are shown in FIG. 19. The concentrations of estradiol in the respective samples ranged from 2 to 23 pg/mL or so. From these results, it has been confirmed that approximately several pg/µL of estradiol can be collected from the skin surface of a forefinger.

Example 5

Quantification of Growth Hormone

1. Collection of Growth Hormone from Skin Surface

Growth hormone was collected from a skin surface in accordance with a similar procedure as in Example 2 except that the collection was conducted from the skin surface of the thumb. The collection of growth hormone was conducted from three subjects.

2. Quantification of Growth Hormone by Enzyme-Linked Immunosorbent Assay (ELIZA)

A sample (100 µL) was recovered in a vial, and was provided for an analysis which employed a commercial ELISA kit ("hGH ELISA", trade name; product of Roche Diagnostics K.K.).

Figure 20:
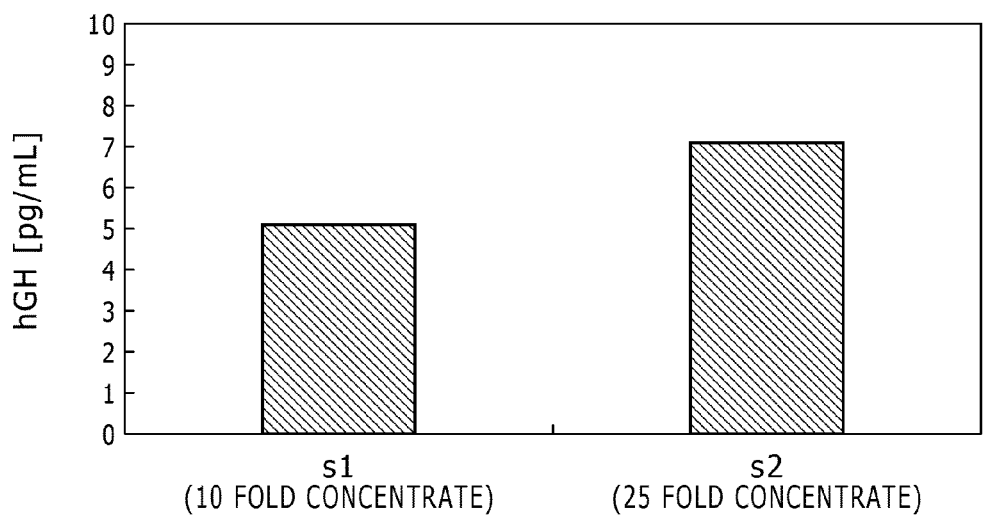
FIG. 20 is a diagram depicting the results of quantitative measurements of growth hormone by enzyme immunoassay (ELISA) (Example 5).

By measuring the standard-brand growth hormone enclosed in the kit, a calibration line was prepared. Using the calibration curve, the concentrations of growth hormone in the samples were calculated. The calculation results are shown in FIG. 20. In the diagram, "s1" indicates a 10-fold concentrate of the sample, and "s2" designates a 25-fold concentrate of the sample. It was possible to collect 0.29 to 0.51 pg/mL of growth hormone from the skin surfaces of the thumbs.

According to the biological information acquisition method and instrument of the present embodiment, a physiologically active substance can be simply, easily and low invasively collected from a living body on a constant basis. The biological information acquisition method and instrument can, therefore, be applied for the sensing of biological information, for example, in the field of health care at home and in the field of entertainment such as games.

The present application contains subject matter related to that disclosed in Japanese priority Patent Application JP2009-111993 filed in the Japan Patent Office on May 1, 2009, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A biological information acquisition method for acquiring information on a living body, the method comprising:
   collecting, on a surface of a solid, a physiologically active substance from a body surface of the living body by causing the physiologically active substance to adhere to the surface of a solid without permeating the solid, wherein no portion of the solid is permeated by the physiologically active substance, wherein collecting the physiologically active substance comprises using a non-invasive technique to collect the physiologically active substance from the body surface;
   inverting the solid;
   applying a stimulus to the inverted solid to release the physiologically active substance from the surface of the solid;
   quantifying an amount of the collected physiologically active substance; and
   determining a physiological state of the living body based, at least in part, on the quantified amount of the collected physiologically-active substance.

2. The biological information acquisition method according to claim 1, wherein the body surface is a skin surface of a finger or palm.

3. The biological information acquisition method according to claim 1, wherein the physiologically active substance is a cortisol, and as the information, information on a stress in the living body is acquired.

4. The biological information acquisition method according to claim 1, wherein the physiologically active substance is a monoamine, and as the information, information on an emotion in the living body is acquired.

5. The biological information acquisition method according to claim 1, wherein the physiologically active substance is an estrogen, and as the information, information on a menstrual cycle of the living body is acquired.

6. The biological information acquisition method according to claim 1, wherein the physiologically active substance is growth hormone, and as the information, information on effects of exercise in the living body is acquired.

7. A physiologically-active substance measurement method comprising:
   collecting, on a surface of a solid, from a body surface of a living body a physiologically active substance originated from the living body by causing the physiologically active substance to adhere to the surface of a solid without permeating the solid, wherein no portion of the solid is permeated by the physiologically active substance, wherein collecting the physiologically active substance comprises using a non-invasive technique to collect the physiologically active substance from the body surface;

inverting the solid; and applying a stimulus to the inverted solid to release the physiologically active substance from the surface of the solid;

quantifying an amount of the physiologically active substance; and determining a physiological state of the living body based, at least in part, on the quantified amount of the collected physiologically active substance.

8. The physiologically-active substance measurement method according to claim 7, wherein the physiologically active substance is at least one physiologically active substance selected from the group consisting of cortisols, monoamines, estrogens and growth hormone.

9. The biological information acquisition method according to claim 1, wherein the solid comprises a plastic plate.

10. The biological information acquisition method according to claim 1, wherein applying a stimulus to the inverted solid comprises applying a solvent to the surface of the solid, wherein the solvent, when applied to the surface of the solid, causes the physiologically active substance to be collected in the solvent.

11. The biological information acquisition method according to claim 1, wherein applying a stimulus to the inverted solid comprises applying a gas to the surface of the solid.

12. The biological information acquisition method according to claim 1, wherein applying a stimulus to the inverted solid comprises oscillating or heating the solid to release the physiologically active substance from the surface of the solid.

13. The physiologically-active substance measurement method according to claim 7, wherein the solid comprises a plastic plate.

14. The physiologically-active substance measurement method according to claim 7, wherein applying a stimulus to the inverted solid comprises applying a solvent to the surface of the solid, wherein the solvent, when applied to the surface of the solid, causes the physiologically active substance to be collected in the solvent.

15. The physiologically-active substance measurement method according to claim 7, wherein applying a stimulus to the inverted solid comprises applying a gas to the surface of the solid.

16. The physiologically-active substance measurement method according to claim 7, wherein applying a stimulus to the inverted solid comprises oscillating or heating the solid to release the physiologically active substance from the surface of the solid.

17. A method, comprising:

collecting, on a surface of a solid, a physiologically active substance from a surface of a living body by causing the physiologically-active substance to adhere to the surface of the solid without permeating the solid, wherein no portion of the solid is permeated by the physiologically active substance, wherein collecting the physiologically active substance comprises using a non-invasive technique to collect the physiologically active substance from the surface of the living body;

inverting the solid;

applying a stimulus to the inverted solid to release the physiologically active substance from the surface of the solid;

quantifying an amount of the collected physiologically active substance; and determining a physiological state of the living body based, at least in part, on the quantified amount of the collected physiologically active substance.

* * * * *